US008981074B2

(12) United States Patent
Kubo et al.

(10) Patent No.: US 8,981,074 B2
(45) Date of Patent: Mar. 17, 2015

(54) LIPID-MODIFIED DOUBLE-STRANDED RNA HAVING POTENT RNA INTERFERENCE EFFECT

(75) Inventors: Takanori Kubo, Hiroshima (JP); Hideki Ohba, Tosu (JP); Hidekazu Toyobuku, Osaka (JP); Hirotake Hayashi, Osaka (JP)

(73) Assignees: National Institute of Advanced Industrial Science and Technology, Tokyo (JP); Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/738,797

(22) PCT Filed: Oct. 24, 2008

(86) PCT No.: PCT/JP2008/069829
§ 371 (c)(1),
(2), (4) Date: Jul. 19, 2010

(87) PCT Pub. No.: WO2009/054551
PCT Pub. Date: Apr. 30, 2009

(65) Prior Publication Data
US 2010/0298411 A1 Nov. 25, 2010

(30) Foreign Application Priority Data
Oct. 24, 2007 (JP) ................................. 2007-276985

(51) Int. Cl.
C07H 21/04 (2006.01)
A61K 47/48 (2006.01)

(52) U.S. Cl.
CPC ..... *A61K 47/48038* (2013.01); *A61K 47/48046* (2013.01)
USPC .......................................... 536/24.5; 514/44

(58) Field of Classification Search
None
See application file for complete search history.

(56) References Cited

U.S. PATENT DOCUMENTS

2003/0206887 A1* 11/2003 Morrissey et al. ........... 424/93.2
2005/0113325 A1* 5/2005 Gryaznov et al. ............... 514/44
2005/0244858 A1* 11/2005 Rossi et al. ...................... 435/6

FOREIGN PATENT DOCUMENTS

WO 2004/065601 A2 8/2004
WO 2006073458 A2 7/2006
WO 2007/022470 A2 2/2007

OTHER PUBLICATIONS

Lorenz et al. Bioorganic & Medicinal Chemistry Letters 2004: 4975-4977.*
Polushin et al. (Nucleic Acids Research 1994: 5492-5496.*
Pongracz et al. (Tetrahedron Letters 40 1999: 7661-7664).*
Christian Wolfrum et al., "Mechanisms and Optimization of in Vivo Delivery of Lipophilic siRNAs", Nature Biotechnology, Oct. 1, 2007, pp. 1149-1157, vol. 25, No. 10, Nature Publishing Group, New York, US.
Daniel De Paula et al., "Hydrophobization and Bioconjugation for Enhanced siRNA Delivery and Targeting", RNA, Apr. 1, 2007, pp. 431-456, vol. 13, No. 4, Published by Cold Spring Harbor Laboratory Press, Woodbury, NY, US.
Takanori Kubo et al., "Modified 27-nt dsRNAs with Dramatically Enhanced Stability in Serum and Long-Term RNAi Activity", Oligonucleotides, Sep. 25, 2007, pp. 445-464, vol. 17, No. 4, Mary Ann Liebert Inc., New York, US.
Takanori Kubo et al., "Chemically Modified Symmetric and Asymmetric Duplex RNAs: An Enhanced Stability to Nuclease Degradation and Gene Silencing Effect", Biochemical and Biophysical Research Communication, Jan. 4, 2008, pp. 54-61, vol. 365, No. 1, Academic Press Inc. Orlando Fl, US.
Andrew Fire et al., "Potent and Specific Genetic Interference by Double-Stranded RNA in *Caenorhabditis elegans*", Nature, Feb. 1998, pp. 806-811, vol. 391, Macmillan Publishers Ltd.
Sayda M. Elbashir et al., "Functional Anatomy of siRNAs for mediating Efficient RNAi in *Drosophila melanogaster* Embryo Lysate", EMBO Journal, 2001, pp. 6877-6888, vol. 20, No. 23.
Dong-Ho Kim et al., "Synthetic dsRNA Dicer Substrates Enhance RNAi Potency and Efficacy", Nature Biotech, Feb. 2005, pp. 222-226, vol. 23, No. 2.
Joao Trindade Marques, et al., "A Structural Basis for Discriminating Between Self and Nonself Double-Stranded RNAs in Mammalian Cells", Nature Biotech, May 2006, pp. 559-565, vol. 24 No. 5.
Christina Lorenz et al., "Steroid and Lipid Conjugates of siRNAs to enhance Cellular Uptake and Gene Silencing in Liver Cells", Bioorganic & Medicinal Chemistry Letters 14, 2004, pp. 4975-4977.

* cited by examiner

*Primary Examiner* — Kimberly Chong
(74) *Attorney, Agent, or Firm* — Sughrue Mion, PLLC

(57) ABSTRACT

An object of the present invention is to provide a novel double-stranded RNA that has high nuclease resistance and high cellular uptake efficiency, and that is capable of producing an excellent RNA interference effect. The present invention provides a lipid-modified double-stranded RNA comprising a sense strand having a nucleotide sequence complementary to a target sequence, and an antisense strand having a nucleotide sequence complementary to the sense strand, the double-stranded RNA being capable of inhibiting the expression of the target gene, the sense strand having a lipid linked to at least one of the first to sixth nucleotides from the 5' end side directly or via a linker.

9 Claims, 11 Drawing Sheets

[RNA] = 500nM

[RNA] = 500nM

LIPID-MODIFIED DOUBLE-STRANDED RNA HAVING POTENT RNA INTERFERENCE EFFECT

CROSS REFERENCE TO RELATED APPLICATIONS

This application is a National Stage of International Application No. PCT/JP2008/069829 filed Oct. 24, 2008, claiming priority based on Japanese Patent Application No. 2007-276985 filed Oct. 24, 2007, the contents of all of which are incorporated herein by reference in their entirety.

TECHNICAL FIELD

The present invention relates to a lipid-modified double-stranded RNA that can efficiently inhibit the expression of a target gene. More specifically, the present invention relates to a lipid-modified double-stranded RNA which has high resistance to nuclease and high cellular uptake efficiency, and produces an excellent RNA interference effect.

BACKGROUND ART

The development of drugs for the efficient treatment of intractable diseases, such as cancer and AIDS, is an important object to be achieved in the life science field. One potential method to achieve this object is using genetic medicines that act only on specific genes. In particular, an RNA interference (RNAi) method using a short double-stranded RNA 21 bases long (small interfering RNA: siRNA) has recently been attracting much attention as such a genetic medicine. The RNAi method was first reported by Fire et al. in 1998 (see Non-Patent Document 1). According to the report of Fire et al., when a double-stranded RNA of about 100 base pairs that is homologous to a specific region of a gene whose function is to be inhibited is introduced into cells, the double-stranded RNA is digested by the action of Dicer into fragments of about 20 to 25 base pairs, and then complexed with a plurality of proteins to form a RNA/protein complex (this complex is referred to as a RISC: a RNA-Induced Silencing Complex), which binds to a homologous site of mRNA produced from the target gene and thereby potently inhibits gene expression. However, it was reported that when a long double-stranded RNA of about 30 base pairs or longer is introduced into mammalian cells, an interferon response, which is an antiviral response, is induced, thus causing the phenomenon of apoptosis. Therefore, it was considered difficult to apply the RNAi method to mammals. Tuschl et al. thus chemically synthesized a 21-base-long double-stranded RNA that has dangling ends at both the 3' ends, and reported that when such a double-stranded RNA is directly introduced into mammalian cells, the double-stranded RNA can potently inhibit gene expression sequence-specifically, while avoiding an interferon response (see Non-Patent Document 2). Tuschl et al. further synthesized short double-stranded RNAs consisting of a double-stranded region of 19 base pairs and dangling end(s) of various lengths at the 3' or 5' ends, and investigated their RNA interference effects. As a result, observations show that 21-base-long siRNA having a dangling end of 2 bases at both the 3' ends demonstrated a very potent RNA interference effect, whereas no other type of short double-stranded RNA exhibited a remarkable RNA interference effect. Based on this report, the RNA interference method using a 21-base-long double-stranded RNA having a dangling end of 2 bases at both the 3' ends is commonly used. The method of inhibiting the expression of a target gene using a short double-stranded RNA 21 bases long is herein referred to as the "siRNA method", to distinguish it from the RNAi method.

Because the siRNA method uses synthetic RNA, sample preparation is comparatively easy, and handling is also easy; furthermore, very potent effects can be produced. Therefore, the siRNA method has been attracting much attention not only in the life science field, but also in the biotechnology business field.

However, this excellent siRNA method also has problem to be solved. As described above, siRNA is composed of an RNA molecule that is readily decomposed by the action of nuclease. Compared to single-stranded RNA, the double-stranded RNA region has a comparatively high resistance to nuclease contained in medium and/or a cell. However, a double-stranded RNA consisting of 19 base pairs scarcely produces the known RNA interference effects. As such, it has been reported that when introduced into cells containing a target gene sequence, although synthetic siRNA produces a potent gene expression-inhibitory effect for about 2 to about 4 days, its RNA interference effect is sharply reduced thereafter, and is almost completely lost in about seven days.

Various chemically modified siRNAs have recently been reported to provide synthetic siRNAs with enhanced cellular uptake efficiency and prolonged, highly active RNA interference effects. For example, to enhance the resistance to exonuclease digestion, siRNAs modified with an amino group, a thiol group, or an abasic site on the end of the siRNA have been synthesized. However, it has been reported that most of the terminally modified siRNAs 21 bases long have remarkably reduced RNA interference effects.

In recent years, J. Rossi et al. reported that a double-stranded RNA of 27 base pairs produces an RNA interference effect that is about 100 times greater than that of a double-stranded RNA of 21 base long (see Non-Patent Document 3). This is presumably because after an RNA of 27 base pairs is cleaved with an RNase III-like enzyme, Dicer, into a 21-base-long siRNA, the protein complex RISC recognizes the siRNA, so that the siRNA effects can be produced with a high efficiency.

As described above, because 27-base long RNA can produce excellent RNA interference effects, expectations to use this RNA as a genetic medicine are increasing. However, the technical method effective for enhancing the RNA interference effect of the 27-base-long RNA is completely unknown. Furthermore, the technical method for enhancing the RNA interference effect of a double-stranded RNA shorter or longer than 27 bases, which has an RNA interference effect, is also unclear.

Double-stranded RNAs having RNA interference effects are generally configured to have dangling ends. RNAs with no dangling ends (i.e., having blunt ends) have also been investigated for their RNA interference effects. The results, however, suggest that the RNA interference effects of double-stranded RNAs blunt-ended on the 5' end side of the sense strand are substantially the same as, or lower than those of double-stranded RNAs having a dangling end on the 5' end side of the sense strand (see Non-Patent Document 4).

Lipids have high cell membrane permeability, and are known to be useful to deliver drugs into cells. Linking such a lipid to a double-stranded RNA having an RNA interference effect is expected to increase the cellular uptake efficiency and thereby produce more potent RNA interference effects. However, it is known that when a lipid is simply linked to a double-stranded RNA having an RNA interference effect, the RNA interference effect is sharply reduced. In the prior art, a lipid-modified double-stranded RNA having both an excellent RNA interference effect and a useful effect based on a lipid had yet to be constructed.

Non-Patent Document 1: Fire et al., Nature, 391, 806-811 (1998)
Non-Patent Document 2: Tuschl et al., EMBO Journal, 20, 6877-6888 (2001)
Non-Patent Document 3: J. Rossi et al., Nature Biotech., 23, 222-226 (2005)
Non-Patent Document 4: J. T. Marques et al., Nature Biotech., 24, 559-565 (2005).

DISCLOSURE OF THE INVENTION

Problem to be Solved by the Invention

An object of the present invention is to provide a novel double-stranded RNA that has high nuclease resistance and high cellular uptake efficiency, and that is capable of producing an excellent RNA interference effect. Another object of the present invention is to provide a pharmaceutical composition containing the novel double-stranded RNA. A further object of the present invention is to provide a method of inhibiting the expression of a target gene, comprising introducing the novel double-stranded RNA into cells to inhibit the expression of the target gene.

Means for Solving the Problem

The present inventors conducted extensive research to achieve the above objects, and found that when a lipid is linked, directly or via a linker, to at least one of the first to sixth nucleotides from the 5' end of a sense strand of a double-stranded RNA comprising can antisense strand having a nucleotide sequence complementary to a target sequence in a target gene, and the sense strand having a nucleotide sequence complementary to the antisense strand, the double-stranded RNA being capable of inhibiting the expression of the target gene, the thus-constructed double-stranded RNA has high nuclease resistance and high cellular uptake efficiency, and produces an excellent RNA interference effect. The present invention was accomplished as a result of further research, based on this finding.

More specifically, the present invention provides the following lipid-modified double-stranded RNA, pharmaceutical compositions containing the novel double-stranded RNA, methods of inhibiting the expression of a target gene, etc.

Item 1. A lipid-modified double-stranded RNA comprising a an antisense strand having a nucleotide sequence complementary to a target sequence in a target gene, and a sense strand having a nucleotide sequence complementary to the antisense strand, the double-stranded RNA being capable of inhibiting expression of the target gene, and the sense strand having a lipid linked to at least one of the first to sixth nucleotides from the 5' end directly or via a linker.

Item 2. A lipid-modified double-stranded RNA according to Item 1 which is blunt-ended on the 5' end side of the sense strand, and is blunt-ended or has a dangling end on the 3' end side of the sense strand.

Item 3. A lipid-modified double-stranded RNA according to Item 1 which has dangling ends on both the 5' and 3' end sides of the sense strand.

Item 4. A lipid-modified double-stranded RNA according to any one of Items 1 to 3 wherein the sense strand consists of 21 to 27 nucleotides.

Item 5. A lipid-modified double-stranded RNA according to Item 2 which is blunt-ended on both the 5' and 3' end sides of the sense strand, and in which each of the sense and antisense strands consists of 27 nucleotides.

Item 6. A lipid-modified double-stranded RNA according to Item 2 which is blunt-ended on both the 5' and 3' end sides of the sense strand, and in which each of the sense and antisense strands consists of 23 nucleotides.

Item 7. A lipid-modified double-stranded RNA according to Item 2 which is blunt-ended on the 5' end side of the sense strand, the sense strand consisting of 25 nucleotides, and the antisense strand consisting of 23 nucleotides.

Item 8. A lipid-modified double-stranded RNA according to Item 3, wherein each of the sense and antisense strands consists of 21 nucleotides.

Item 9. A lipid-modified double-stranded RNA according to any one of Items 1 to 8, wherein the lipid is a fatty acid having 6 to 50 carbon atoms.

Item 10. A lipid-modified double-stranded RNA according to any one of Items 1 to 9, wherein the lipid is lauric acid, stearic acid, myristic acid, or palmitic acid.

Item 11. A lipid-modified double-stranded RNA according to any one of Items 1 to 10, wherein the lipid is linked to at least one of the first to sixth nucleotides from the 5' end of the sense strand via a linker, the linker being represented by the structural formula

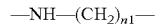   (L-4)

wherein n1 is an integer of 1 to 40.

Item 12. A pharmaceutical composition comprising the lipid-modified double-stranded RNA of any one of claims 1 to 10 and a pharmaceutically acceptable base.

Item 13. Use of the lipid-modified double-stranded RNA of any one of Items 1 to 10 for the production a pharmaceutical composition in order to inhibit the expression of a target gene.

Item 14. A method of inhibiting the expression of a target gene comprising introducing a lipid-modified double-stranded RNA of any one of claims 1 to 10 into cells to inhibit the expression of the target gene.

Effect of the Invention

The lipid-modified double-stranded RNA of the present invention is modified with a lipid in the 5' end side of the sense strand, thereby producing a significantly increased RNA interference effect. More specifically, the lipid-modified double-stranded RNA has a lipid linked to a specific site of the RNA, and thus has remarkably enhanced resistance to nuclease and cellular uptake efficiency, without impairing Dicer processing or the binding of RNA to RISC, and thus can greatly contribute to medical use.

The lipid-modified double-stranded RNA of the present invention has excellent ability of intracellular delivery, even when used alone. Therefore, the lipid-modified double-stranded RNA can be introduced into cells without the use of any known gene transfection reagents, or using a known gene transfection reagent in a reduced amount. Therefore, the lipid-modified double-stranded RNA of the present invention can inhibit the expression of cytotoxicity, which is a concern when using known gene transfection reagents, thereby ensuring a high degree of safety in clinical applications.

Thus, the expression of the target gene can be more effectively inhibited or impaired by using the pharmaceutical composition of the present invention or by using the method of inhibiting the expression of a target gene according to the present invention.

BEST MODE FOR CARRYING OUT THE INVENTION

In this specification, the "blunt end" or "blunt-ended" refers to a terminal structure of a double-stranded RNA in which bases in the terminal region of a sense strand and bases in the terminal region of an antisense strand complementary to the sense strand are paired without forming a single strand. The "dangling end" refers to a terminal portion of a nucleotide sequence in which a single strand is present without forming a double strand, because complementary bases are not present in the terminal region of the sense strand of the double-stranded RNA or the terminal region of the antisense strand complementary to the sense strand.

The lipid-modified double-stranded RNA of the invention comprises a sense strand having a nucleotide sequence complementary to a target sequence in a target gene.

The target gene herein refers to a gene whose expression is to be inhibited by the RNA interference effect. The target gene of the lipid-modified double-stranded RNA of the invention is not particularly limited, and can be suitably selected according to the intended use of the lipid-modified double-stranded RNA.

The target sequence in the target gene is not particularly limited as long as the expression of the gene can be inhibited by RNA interference effects. The target sequence can be suitably determined according to a known method, for example, using an NCBI BLAST search, etc. For example, the target sequence may be a region consisting of 19 to 30 bases following the bases "AA" in the exon region 50 to 100 bases downstream of the start codon of the coding region (ORF) of the target gene, and having a GC content of about 50%. It is experientially known in this field that excellent RNA interference effects can be obtained using a strand complementary to such a target sequence. For example, the target sequence can be determined according to the instructions of IDT (Integrated DNA Technologies, Inc.; Dicer Substrate RNAi Design). A recent report revealed that a double-stranded RNA having high RNA interference effects can be produced by constructing a double-stranded RNA which has: (i) an A/U pair on the 5' end side of the antisense strand; (ii) a G/C pair on the 5' end side of the sense strand; and (iii) about five A/U pairs on the 5' end side of the antisense strand; (iv) and does not have nine or more G/C pairs (Ui-Tei et al., Nucleic Acids Res., 32, 936-948 (2004)).

When the antisense strand of the lipid-modified double-stranded RNA of the invention does not have a dangling end, the antisense strand consists of a nucleotide sequence complementary to the target sequence. When the antisense strand has a dangling end at the 5' end and/or the 3' end, the antisense strand consists of a nucleotide sequence having a nucleotide sequence complementary to the target sequence, and a nucleotide sequence of the dangling end linked to the 5' end and/or the 3' end of the complementary nucleotide sequence.

As long as the RNA interference effect can be achieved, the number of nucleotides that constitute the antisense strand of the lipid-modified double-stranded RNA of the invention is not particularly limited, and can be suitably determined according to the desired structure of the double-stranded RNA. The number of nucleotides is usually 21 to 27, preferably 21, 23, 25, or 27, and more preferably 21, 23, or 27. When the antisense strand does not have a dangling end, the number of nucleotides that constitute the antisense strand herein means the total number of nucleotides constituting the nucleotide sequence complementary to the target sequence. When the antisense strand has a dangling end, the number of nucleotides that constitutes the antisense strand means the sum of the number of nucleotides constituting the dangling end and the number of nucleotides constituting the nucleotide sequence complementary to the target sequence. The lipid-modified double-stranded RNA of the invention comprises a sense strand having a nucleotide sequence complementary to the antisense strand.

When the sense strand of the lipid-modified double-stranded RNA of the invention does not have a dangling end, the sense strand consists of a nucleotide sequence complementary to a part or all of the "nucleotide sequence complementary to a target sequence" of the antisense strand. When the sense strand has a dangling end at the 5' end and/or the 3' end, the antisense strand consists of: a nucleotide sequence complementary to a part or all of the "nucleotide sequence complementary to a target sequence" of the antisense strand; and a nucleotide sequence of the dangling end linked to the 5' end and/or the 3' end of the complementary nucleotide sequence of the sense strand. As long as the RNA interference effect can be achieved, the number of nucleotides that constitute the sense strand in the lipid-modified double-stranded RNA of the invention is not particularly limited, and can be suitably determined according to the desired structure of the double-stranded RNA. The number of the nucleotides is usually 21 to 27, preferably 21, 23, 25, or 27, and more preferably 21, 23, or 27. When the sense strand does not have a dangling end, the number of nucleotides that constitute the sense strand means the total number of nucleotides constituting the nucleotide sequence complementary to the target sequence. When the sense strand has a dangling end, the number of nucleotides that constitute the sense strand means the sum of the number of nucleotides constituting the dangling end, and the number of nucleotides constituting the nucleotide sequence complementary to the target sequence.

The nucleotides that constitute the sense strand and the antisense strand of the lipid-modified double-stranded RNA of the invention are basically ribonucleotides. To enhance the resistance to enzymatic digestion, the RNA sequence may contain various chemically modified nucleotides, such as 2'-O-methyl-modified nucleotides, 2'-F-modified nucleotides, LNA (Locked Nucleic Acid) nucleotides, deoxyribonucleotides, or the like. Particularly, when the lipid-modified double-stranded RNA of the invention has a dangling end, the dangling end of the sense strand and/or the antisense RNA may be composed of deoxyribonucleotides. Examples of such chemically modified nucleotides include phosphate backbone-modified nucleotides such as phosphorothioate-modified DNA/RNA and boranophosphate-modified DNA/RNA; 2'-modified nucleotides such as 2'-OMe-modified RNA and 2'-F-modified RNA; modified nucleotides obtained by crosslinking a sugar molecule of a nucleotide, such as LNA (Locked Nucleic Acid) and ENA (2'-O,4'-C-ethylene-bridged nucleic acids); modified nucleotides having different backbones, such as PNA (Peptide Nucleic Acid) and morpholine-nucleotide; base-modified nucleotides such as 5-fluorouridine and 5-propyluridine; and the like.

The lipid-modified double-stranded RNA of the invention is not particularly limited structurally, as long as the sense and antisense strands are hybridized into a double strand. For example, the lipid-modified double-stranded RNA preferably has the following structure: a structure (A) in which the double-stranded RNA is blunt-ended (i.e. has a blunt end) on the 5' end side of the sense strand, and is blunt-ended or has a dangling end (single-stranded region) on the 3' end side of the sense strand; a structure (B) in which the double-stranded RNA has dangling ends on the 5' and 3' end sides of the sense strand. The structure in which the double-stranded RNA has a dangling end on the 3' end side of the sense strand includes cases when the 3'-end region of the sense strand forms a dangling end, and cases when the 5'-end region of the antisense strand forms a dangling end. The structure in which the double-stranded RNA has a dangling end on the 5' end side of the sense strand includes the case in which the 5' end region of the sense strand forms a dangling end, and the case in which the 3' end region of the antisense strand forms a dangling end.

Among the double-stranded RNAs that can be used to form the lipid-modified double-stranded RNA of the invention, double-stranded RNAs having the structures (A-1) to (A-3) shown below are particularly preferable among those having the above structure (A), and double-stranded RNAs of the structure (B-1) shown below are particularly preferable among those having the above structure (B) to achieve a further enhanced RNA interference effect. The structure (A-1), in which the double-stranded RNA is blunt-ended on both the 5' and 3' end sides of the sense strand, and each of the sense and antisense strands consists of 27 nucleotides; the structure (A-2), in which the double-stranded RNA is blunt-ended on both the 5' and 3' end sides of the sense strand, and each of the sense and antisense strands consists of 23 nucleotides, respectively; the structure (A-3), in which the double-stranded RNA is blunt-ended on the 5' end side of the sense strand, and the sense strand consists of 25 nucleotides, and the antisense strand consists of 23 nucleotides; and the structure (B-1), in which the double-stranded RNA has dangling ends each consisting of two nucleotides on both the 3' end of the sense strand and the 3' end of the antisense strand, and each of the sense and antisense strands consists of 21 nucleotides.

More specifically, in the structures (A-1) and (A-2), sense and antisense strands are hybridized without no dangling end formed on the ends. In the structure (A-3), sense and antisense strands are hybridized so that the double-stranded RNA is blunt-ended on the 5' end of the sense strand, and the first and second nucleotides from the 3' end of the sense strand form a dangling end. The structure (B-1) is that the first to 19th nucleotides from the 5' end of the sense strand and the third to 21st nucleotides from the 3' end of the antisense strand are hybridized so that the first and second nucleotides from the 3' end of the sense strand, and the first and second nucleotides from 3' end of the antisense strand form dangling ends, respectively.

The lipid-modified double-stranded RNA of the invention has at least one lipid linked to at least one of the first to sixth nucleotides from the 5' end of the sense strand. The lipid-modified double-stranded RNA of the invention has no substitutents at any other position than the 5' end region of the sense strand. More specifically, no substituents are present in any other area than the 5' end region of the sense strand and in the antisense strand, and these areas consist of nucleotides. Linking lipid(s) only to the 5' end region of the sense strand can enhance cellular uptake efficiency and provide a remarkably excellent RNA interference effect.

The lipid linked to the sense strand of the lipid-modified double-stranded RNA of the invention is not particularly limited, and examples thereof include simple lipids (esters of fatty acids with various alcohols); complex lipids such as phospholipids and glycolipids; derived lipids such as fatty acids, higher alcohols, lipid soluble vitamins, steroids, and hydrocarbons. To enhance the cellular uptake efficiency and the RNA interference effect, the lipid used is preferably a derived lipid, more preferably a fatty acid having 6 to 50 carbon atoms, still more preferably a fatty acid having 10 to 22 carbon atoms, particularly preferably a fatty acid having 12 to 18 carbon atoms, more particularly preferably lauric acid, stearic acid, myristic acid, or palmitic acid, and most preferably palmitic acid.

The manner of linking of the lipid to the sense strand to form the lipid-modified double-stranded RNA of the invention is not particularly limited. The lipid may be linked directly or via linker to the sense strand. In the present invention, the linker via which the lipid is linked to the sense strand is not the linker consisting of nucleic acid. The linker is not particularly limited as long as the lipid and the sense strand can be linked therethrough. For example, linkers having the following structures can be used as the linker:

  (L-1)

  (L-2)

  (L-3)

  (L-4)

  (L-5)

  (L-6)

  (L-7)

  (L-8)

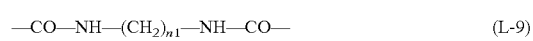  (L-9)

  (L-10)

  (L-11)

  (L-12)

  (L-13)

  (L-14)

  (L-15)

  (L-16)

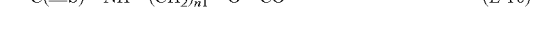  (L-17)

  (L-18)

  (L-19)

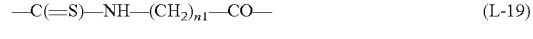  (L-20)

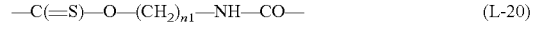  (L-21)

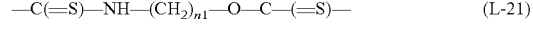  (L-22)

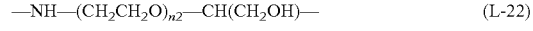  (L-23)

In the above Formulas (L-4) to (L-21), n1 is an integer of 1 to 40, preferably an integer of 2 to 20, and more preferably an integer of 2 to 12.

In the above Formulas (L-22) and (L-23), n2 is an integer of 1 to 20, preferably an integer of 1 to 10, and more preferably an integer of 1 to 6.

The linkers of Formulas (L-4) to (L-23) may link the sense strand on either the left or right side. Preferably, a specific site of the sense strand (or the nucleic acid of nucleic acid conjugate) is linked on the right side of the linkers of Formulas (L-4) to (L-23), and a lipid is linked on their left side.

The linking site of the lipid to the linker may be appropriately selected according to the types of lipid and linker used. For example, when a fatty acid is used as the lipid, it can be linked via an ester bond, an amide bond, or like bond formed between the carboxyl group of the fatty acid and the linker. More specifically, when a fatty acid is used as the lipid, the lipid is preferably linked by substitution of —OH of the carboxyl group of the fatty acid with the linker.

The linker is suitably selected according to the type of lipid to be linked. When a fatty acid is used as the lipid, the linkers represented by Formula (L-4) are preferably used.

In addition to the above-mentioned linkers, other linkers are also usable. Examples thereof include bifunctional linkers (linkers containing two functional groups), such as N-succinimidyl=3-(2-pyridyldithio)propionate, N-4-maleimide butyric acid, S-(2-pyridyldithio)cysteamine, iodoacetoxysuccinimide, N-(4-maleimidebutyloxy) succinimide, N-[5-(3'-maleimide propylamide)-1-carboxypentyl]iminodiacetic acid, N-(5-aminopentyl)-iminodiacetic acid, and the like. In the sense strand, the nucleotide linked to the lipid or to the linker used for linking the lipid is not particularly limited, as long as it is at least one of the first to sixth nucleotides from the 5' end of the sense strand, preferably at least one of the first to fourth nucleotides from the 5' end, more preferably the first and/or second nucleotide from the 5' end, and particularly preferably the nucleotide on the 5' end (the first nucleotide from the 5' end).

The linking site of the sense strand to the lipid or to the linker used for linking the lipid is not particularly limited. It is preferably linked by substitution of the hydrogen atom of the hydroxyl group of the phosphoric acid portion of a specific nucleotide of the sense strand.

The number of lipids linked to the lipid-modified double-stranded RNA of the invention is not particularly limited. For example, one to three lipids, preferably one or two lipids, and more preferably one lipid can be linked.

The lipid-modified double-stranded RNA of the invention can be produced by synthesizing a sense strand having at least one lipid linked thereto, and an antisense strand, respectively, and hybridizing the sense and antisense strands according to known methods. The sense strand having a lipid linked thereto can also be produced according to known synthetic methods.

The modified double-stranded RNA of the invention can be introduced into cells to inhibit or impair the expression of a target gene, and therefore can be used as a pharmaceutical for inhibiting or impairing the expression of a target gene or a composition for gene therapy, i.e., a pharmaceutical composition. The pharmaceutical composition of the invention can be formulated into various dosage forms. Examples of dosage forms of the pharmaceutical composition of the invention include liquid preparations such as liquids (such as syrups), drops, and injections; solid preparations such as tablets, pills, powders, granules, and capsules (such as soft capsules); and the like. When the pharmaceutical composition of the invention is a liquid preparation, the composition may be cryopreserved, or preserved after removing water therefrom by lyophilization, etc. Lyophilized preparations and dry syrups, etc. may be used in the form of solutions by adding distilled water for injection, sterile water or the like when used. When the pharmaceutical composition of the invention is a solid preparation, the composition may be used in the form of a solution by adding distilled water for injection, sterile water, or the like, when used.

The pharmaceutical composition may consist of a lipid-modified double-stranded RNA alone, or may further contain a pharmaceutically acceptable carrier, if necessary. The carrier to be used is not particularly limited as long as it does not impair the target gene expression inhibitory effect of the modified double-stranded RNA of the invention, and can be suitably selected according to the dosage form. Examples of carriers that can be used include purified water, aqueous sugar solutions, buffers, physiological saline, aqueous polymer solutions, RNase-free water, etc. When the pharmaceutical composition of the invention contains the carrier, the proportions of these components in the composition are not particularly limited, as long as they do not impair the target gene expression inhibitory and impairing effects of the modified double-stranded RNA of the invention, and can be suitably selected according to the dosage form.

For example, the pharmaceutical composition of the invention may contain the modified double-stranded RNA in an amount of 0.001 to 50, more preferably 0.01 to 10, and still more preferably 0.1 to 1. The pharmaceutical composition of the invention may contain the carrier in an amount of 50 to 99.999 wt. %, preferably 90 to 99.99 wt. %, and still more preferably 99 to 99.9 wt. %, based on the total weight of the composition.

The target gene and disease for which the pharmaceutical composition of the invention is used are not particularly limited. The relationship between the target gene and the disease is known. The type of cell into which the pharmaceutical composition of the invention is introduced is not limited. The cells to be used may be human-derived cells or non-human, animal-derived cells. The pharmaceutical composition of the invention may be used in vitro or in vivo.

The amount and method of introducing the lipid-modified double-stranded RNA of the invention into cells are the same as in conventional siRNA methods. For example, when the pharmaceutical composition of the invention is used to introduce the lipid-modified double-stranded RNA into cells in vitro, a method of culturing cells in the presence of an appropriate amount of the pharmaceutical composition can be used. When the pharmaceutical composition of the invention is used to introduce the lipid-modified double-stranded RNA into cultured cells or cells extracted from the living body in vitro, the lipid-modified double-stranded RNA of the invention may be introduced in the presence of serum. When the pharmaceutical composition of the invention is used to introduce the lipid-modified double-stranded RNA into cells in vivo, direct injection of the pharmaceutical composition into the tissue; intravenous, subcutaneous, muscular, interperitoneal, intraocular, gastrointestinal or dental injection; inhalation administration into the nasal cavity, oral cavity, lung, or the like; oral administration; transdermal administration through the skin; transmucosal administration through the oral mucosa, vaginal mucosa, ocular mucosa, rectal mucosa, and uterine mucosa; and like methods can be used.

When the pharmaceutical composition of the invention is used, a known gene transfection reagent used to transfect siRNA into cells may be optionally used together. Alternatively, the pharmaceutical composition of the invention may contain a gene transfection reagent. The lipid-modified double-stranded RNA contained in the pharmaceutical composition of the invention has excellent cellular transfection abilities, even when used alone. Therefore, the lipid-modified double-stranded RNA can be introduced into cells without using a known gene transfection reagent used to deliver siRNA into cells, or using a gene transfection reagent in a reduced amount.

The pharmaceutical composition of the invention can be used in an effective amount, for example, an amount such that the lipid-modified double-stranded RNA is introduced in an amount of 0.001 to 10 pM, preferably 0.001 to 1 pM, and more preferably 0.01 to 0.1 pM, per cell.

The pharmaceutical composition of the invention can inhibit or impair the expression of a target gene to thereby prevent, ameliorate, or treat a disease caused by the expression of the target gene.

The present invention further provides a method of inhibiting the expression of a target gene. The method of inhibiting the expression of a target gene comprises transfecting the lipid-modified double-stranded RNA into cells.

The target gene or disease is not particularly limited, and the relationship between the target gene and the disease is known, as mentioned above. The type of cell into which the modified double-stranded RNA of the invention is introduced is not limited. The cells to be used may be human-derived cells or non-human animal cells. The modified double-stranded RNA of the invention may be introduced in vitro or in vivo.

In the method of inhibiting the expression of a target gene of the invention, the amount and method of introducing the lipid-modified double-stranded RNA of the invention into cells are the same as in conventional siRNA methods, and can be suitably selected. For example, in the method of inhibiting the expression of a target gene of the invention, to introduce the lipid-modified double-stranded RNA of the invention into cells in vitro, a step of culturing cells in the presence of an appropriate amount of the lipid-modified double-stranded RNA can be used. In the method of inhibiting the expression of a target gene of the invention, to introduce the lipid-modified double-stranded RNA into cultured cells or cells extracted from the living body in vitro, a step of introducing the lipid-modified double-stranded RNA of the invention into cells in the presence of serum can be used. In the method of inhibiting the expression of a target gene of the invention, to introduce the lipid-modified double-stranded RNA into cells in vivo, a step as described followed can be used; direct injection of the lipid-modified double-stranded RNA of the invention into the tissue; intravenous, subcutaneous, muscular, interperitoneal, intraocular, gastrointestinal, dental or like injection; inhalation administration into the nasal cavity, oral cavity, lung or the like; oral administration; transdermal administration through the skin; transmucosal administration through the oral mucosa, vaginal mucosa, ocular mucosa, rectal mucosa, and uterine mucosa; and like steps. By bringing an effective amount of the lipid-modified double-stranded RNA into contact with the cells, the lipid-modified double-stranded RNA of the invention can be introduced into cells. For example, the lipid-modified double-stranded RNA is administered in an amount of 0.001 to 10 pM, preferably 0.001 to 1 pM, and more preferably 0.01 to 0.1 pM, per cell.

The lipid-modified double-stranded RNA of the invention has excellent cellular transfection ability, even when used alone. Therefore, the lipid-modified double-stranded RNA can be introduced into cells without using a known gene transfection reagent, or using a gene transfection reagent in a reduced amount.

The method of inhibiting the expression of a target gene according to the present invention can inhibit or impair the expression of the target gene to thereby prevent, ameliorate, or treat a disease caused by the expression of the target gene.

EXAMPLES

The present invention is described in detail with reference to the following Examples; however, the invention is not limited by these Examples.

Example 1

Inhibitory Effects of 5' Lipid-Modified Double-Stranded RNAs on the Expression of the Luciferase Gene 1. Synthesis of Lipid-Modified Double-Stranded RNAs Targeting the Luciferase Gene 1-1. Sequences of Sense Strands and Antisense Strands Double-stranded RNAs containing 21- to 27-base-long sense strands and 21- to 27-base-long antisense strands were designed having a sequence homologous to *Renilla* luciferase and capable of suppressing the expression of the *Renilla* luciferase gene. Such double-stranded RNAs can produce various forms of double strands, depending on the combination of the antisense strand and the sense strand. The following names were assigned to these double-stranded RNAs. "DS (double-stranded) RNAs": completely double-stranded RNAs not containing a dangling end (a single-stranded region) (i.e., double-stranded RNAs containing blunt ends on both of the 5' and 3' end sides of the sense strand); "Si RNAs": double-stranded RNAs containing dangling ends (overhang) on both end sides thereof; and "RO (Right Overhang) RNAs": double-stranded RNAs containing a dangling end only on the right side when the 5' end side of the sense strand is shown on the left side. The names of these various double-stranded RNAs are distinguished by designating the sense strand as "A" ("A1" or "A2") and the antisense strand as "B", and by indicating the number of bases of each single-stranded RNA, i.e., the sense strand and antisense strand. Because two types of sense strands were designed, they are each designated as "A1" and "A2" for classification. As for the double-stranded RNAs modified with a lipid at the 5' end region of the sense strand, the designation "Cx (x=16 or 12)" is given after the name of each sense strand. The sequences of the RNAs used are as follows.

```
Sense Strands:
                                              (SEQ ID NO: 1)
27nt 27A1:    5'-CUGGCCUUUCACUACUCCUACGAGCAC-3'

(SEQ ID NO: 2)
25nt 25A1:    5'-CUGGCCUUUCACUACUCCUACGAGC-3'

(SEQ ID NO: 3)
23nt 23A1:    5'-CUGGCCUUUCACUACUCCUACGA-3'

(SEQ ID NO: 4)
21nt 21A1:    5'-CUGGCCUUUCACUACUCCUAC-3'

(SEQ ID NO: 5)
21nt 21A2:    5'-GGCCUUUCACUACUCCUACGA-3'

Antisense Strands:.
                                              (SEQ ID NO: 6)
27nt 27B:     5'-GUGCUCGUAGGAGUAGUGAAAGGCCAG-3'

(SEQ ID NO: 7)
25nt 27B:     5'-GCUCGUAGGAGUAGUGAAAGGCCAG-3'

(SEQ ID NO: 8)
23nt 27B:     5'-UCGUAGGAGUAGUGAAAGGCCAG-3'

(SEQ ID NO: 9)
21nt 27B:     5'-GUAGGAGUAGUGAAAGGCCAG-3'
```

1-2. Synthesis of Lipid-Unmodified Double-Stranded RNAs Targeting the Luciferase Gene Various double-stranded RNAs were prepared using the sense strands and antisense strands listed above. Each double-stranded RNA was prepared by mixing equimolar amounts of a sense strand and an antisense strand in a universal buffer (Hayashi Kasei Co., Ltd.), heating the mixture at 92° C. for 2 minutes, and then gradually reducing the temperature to 4° C. The resulting various double-stranded RNAs were electrophoresed on a 20% polyacrylamide gel at 250 V for 60 minutes, and then confirmed by dying with a silver staining kit (GE Health Care Bioscience). FIG. 1A shows the structures of the unmodified double-stranded RNAs.

1-3. Synthesis of Lipid-Modified Double-Stranded RNAs Targeting the Luciferase Gene Lipid-modified sense strands in which a lipid was linked to the 5' end of the sense strands of the double-stranded RNAs capable of inhibiting the expression of the luciferase gene were synthesized. In these lipid-modified sense strands, the lipid was covalently attached via an aminoalkyl group (Amino Modifier C6; Glen Research) linked to the 5' end of the above-mentioned sense strands. The lipid-modified sense strands were synthesized by reacting in a liquid phase a lipid compound containing an active ester group (hereinafter referred to as an "active ester-containing lipid compound" with a sense strand modified by amination of the 5' end (Reaction Schemes 1 and 2).

Reaction Scheme 1

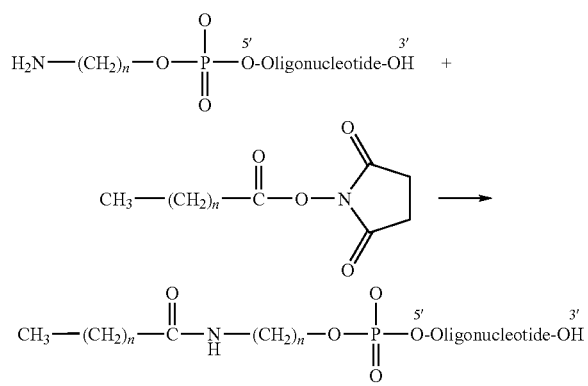

Reaction Scheme 2

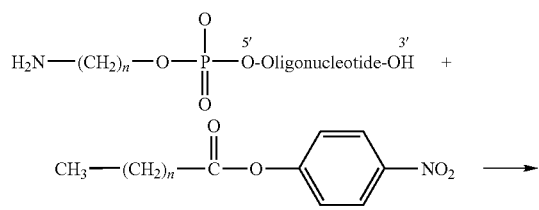

-continued

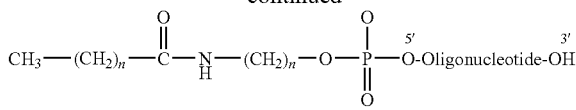

A specific synthetic process is described below. To aminate the 5' end of the sense strand, a conventional process (the phosphoramidite synthetic process) may be performed using 5'-Amino-Modifier C6 (Glen Research) on RNA solid phase synthesis, to thereby synthesize a sense strand modified with an aminoalkyl group at the 5' end (21 bases in length). The sense strand modified with an aminoalkyl group at the 5' end, which had been purified by HPLC and subjected to MALDI-TOF MS analysis, was purchased from Hayashi Kasei Co., Ltd. The resulting sense strand modified with an aminoalkyl group at the 5' end has $-(CH_2)_6-NH_2$ linked to the 5' end (the phosphate residue of the first nucleotide from the 5' end). The concentration of the resulting single-stranded RNA was determined by measuring the absorbance at 260 nm using a UV spectrometer. The single-stranded RNA modified with the aminoalkyl group was mixed with an active ester-containing lipid compound (palmitic acid N-hydroxysuccinimide ester (Sigma-Aldrich), or lauric acid-4-nitrophenyl ester (TCI)) dissolved in DMF (N,N dimethylformamide) under condensation conditions to synthesize a lipid-modified sense strand. After the reaction, the reaction solution was purified by HPLC to remove unwanted reagents in the reaction solution containing the lipid-modified sense strand. HPLC purification was performed with Buffer A: 100% 20 mM TEAA (pH 7.0) and Buffer B: 70% $CH_3CN$/20 mM TEAA (pH 7.0) at a linear gradient of 10-100% Buffer B over a period of 50 minutes. CAP CELL (4.6×150 mm, 5 μm; Shiseido) was used as the purification column. FIG. 2 shows exemplary HPLC analytical results. The lipid-modified sense strand purified by HPLC was lyophilized and dissolved in purified water, after which the concentration and synthetic yield thereof were determined by UV spectral analysis.

The structural models and yields of the resulting lipid-modified sense strands are as follows.

27A1C16:

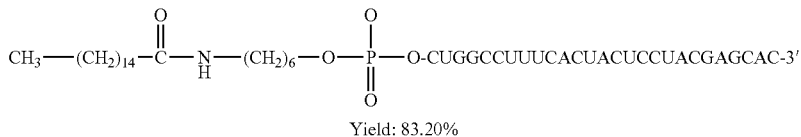

Yield: 83.20%

27A1C12:

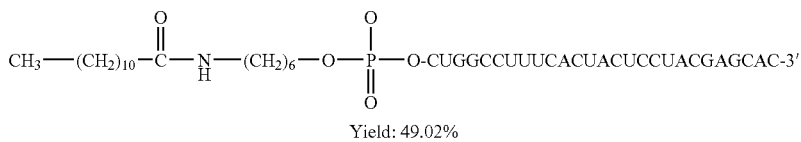

Yield: 49.02%

25A1C16:

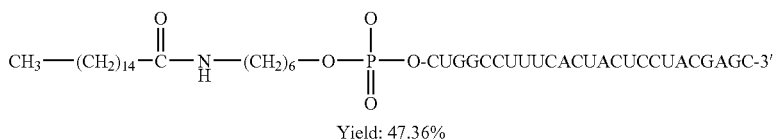

Yield: 47.36%

23A1C16:

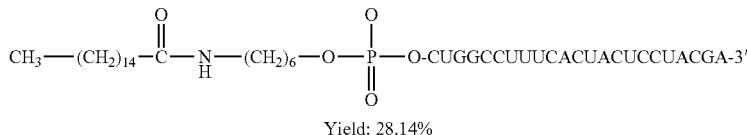

Yield: 28.14%

21A1C16:

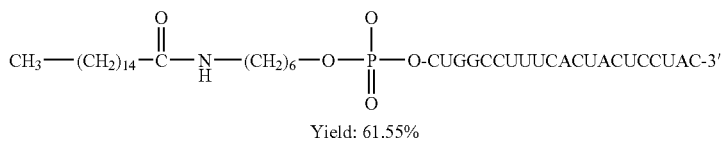

Yield: 61.55%

21A2C16:

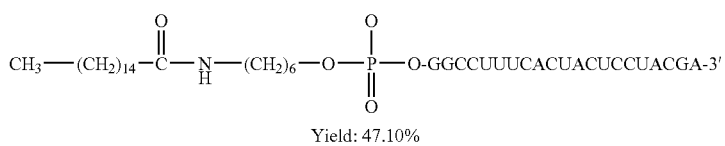

Yield: 47.10%

21A2C12:

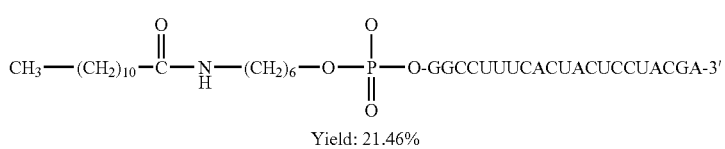

Yield: 21.46%

The resulting lipid-modified sense strands were paired with the antisense strands to produce lipid-modified double-stranded RNAs. The double-stranded RNAs were formed according to the same procedure as described above, and confirmed by 20% polyacrylamide gel electrophoresis. FIG. 1B shows the structures of the lipid-modified double-stranded RNAs. In FIG. 1B, X is 16 when a palmitic acid derivative is linked, and X is 12 when a lauric acid derivative is linked.

2. Degradative Enzyme Resistance of Lipid-Modified Double-Stranded RNAs

The nuclease resistance of lipid-modified 27 nt dsRNA (Ds 27A1C16/27B) was evaluated. First, 27 nt dsRNA modified with a lipid at the 5' end of the sense strand, adjusted to a final concentration of 2 µM, was incubated at 37° C. in an RPMI-1640 medium (Invitrogen) containing 10% FBS (Sanko Junyaku, Co., Ltd.) (final volume: 110 µl). After 0 h, 0.5 h, 1 h, 2 h, 4 h, 6 h, 8 h, 12 h, 24 h, and 48 h, each 10 µl aliquot was sampled and inserted into a sample tube containing 2 µl of a loading die. In order to subsequently stop the degradation reaction, the sample taken was rapidly lyophilized in liquid nitrogen and preserved at −20° C. The resulting sample product was electrophoresed on a 20% polyacrylamide gel at 250 V for 70 minutes. The product was then dyed with a silver staining kit (GE Health Care Bioscience) (see the product manual for staining conditions), and subjected to gel analysis on a ChemiImager 4000 (Alpha Innotech Corporation). As comparisons, 21-base-long 21siRNA (si 21A2/21B), which is generally in wide use, and unmodified 27 nt dsRNA (Ds 27A1/27B) were similarly evaluated for their nuclease resistance. FIG. 3 shows the results of the gel electrophoresis.

As a result, the 21siRNA was rapidly degraded in the serum-containing medium, and disappearance thereof was confirmed in about 1 to 2 hours. On the other hand, the unmodified 27 nt dsRNA and lipid-modified 27 nt dsRNA had nuclease resistance much higher than that of the 21siRNA, and these double-stranded RNAs still remained even after 48 hours. These results led to a new finding that the lipid-modified double-stranded RNA possessed in vivo stability markedly higher than that of the 21siRNA that is generally in wide use.

3. Processing by Dicer of Lipid-Modified Double-Stranded RNAs Targeting the Luciferase Gene Processing by recombinant Dicer of the synthesized double-stranded RNAs and lipid-modified double-stranded RNAs was evaluated. The Dicer cleavage experiments were performed as follows. Ten microliters of 0.5 U recombinant Dicer (Gene Therapy Systems) and unmodified double-stranded RNAs or lipid-modified double-stranded RNAs adjusted to a final concentration of 2 µM in solutions of 20 mM Tris-HCl (pH 8.0), 15 mM NaCl, and 2.5 mM $Mg_2Cl$ were prepared in sample tubes, and then the samples were incubated in an incubator at 37° C. for 12 hours. In order to subsequently stop the cleavage reactions by Dicer, 2 µl of Dicer Stop Solution (Gene Therapy Systems) was added into the reaction solutions, followed by the addition of 2 µl of a loading die. The resulting sample products were electrophoresed on a 20% polyacrylamide gel at 250 V for 70 minutes. The products were then dyed with a silver staining kit (GE Health Care Bioscience) (see the product manual for staining conditions), and subjected to gel analysis on a ChemiImager 4000 (Alpha Innotech corporation). As a control, unmodified 21siRNA (si21A2/21B) was also analyzed by gel electrophoresis. The results are shown in FIG. 4.

The results showed that, among the double-stranded RNAs in which the sense strands of Ds RNAs (Ds 27A1/27B, Ds 25A1/25B, Ds 23A1/23B, and Ds 21A1/21B) were modified with a lipid, bands were observed with Ds 27A1C16/27B and Ds 27A1C12/27B in similar positions to the unmodified 21siRNA by the action of recombinant Dicer, thus strongly indicating the production of 21-base-long siRNAs containing a dangling end of two bases by Dicer cleavage. Also with Ds 25A1C16/25B and Ds 23A1C16/23B, new bands were observed in similar positions to the 21siRNA in the presence of Dicer, revealing that they were processed by Dicer. With Ds 21A1C16/21B, on the other hand, no significant change was observed in the presence of Dicer, revealing that it was not processed by Dicer.

Moreover, processing by Dicer of the double-stranded RNAs in which the sense strands of RO RNAs (RO 27A1/25B, RO 25A1/23B, RO 23A1/21B, and RO 21A1/19B) each containing a dangling end of two bases on the 3' end region of the sense strand were modified with a lipid, was similarly evaluated. As a result, with the three types, i.e., RO 27A1C16/25B, RO 25A1C16/23B, and RO23A1C16/21B, bands were observed in similar positions to the 21siRNA in the presence of Dicer, revealing that they were processed by Dicer. RO 27A1C16/25B and RO 25A1C16/23B, in particular, demonstrated significant processing effects by Dicer. With the relatively short RO 21A1C16/19B, on the other hand, no change was observed in the double-stranded RNA even in the presence of Dicer, suggesting that it was not processed by Dicer.

Furthermore, processing by Dicer of double-stranded RNAs in which the sense strands of the RO RNAs (RO 27A1/23B and RO 25A1/21B) containing a dangling end of four bases on the 3' end region of the sense strand were modified with a lipid, as well as a double-stranded RNA in which the sense strand of the RO RNA (RO 27A1/21B) containing a dangling end of six bases on the 3' end region of the sense strand was modified with a lipid, was evaluated. As a result, all of the aforementioned RO RNAs were processed by Dicer, and new bands were observed in the same positions as the 21 nt siRNA.

Furthermore, processing by Dicer of double-stranded RNAs in which the sense strands of the RO RNAs (RO 25A1/27B, RO 23A1/25B, and RO 23A1/27B) containing a dangling end on the 5' end region of the antisense strand were modified with a lipid was similarly evaluated. As a result, with some of the lipid-modified RO RNAs containing a dangling end on the 5' end region of the antisense strand, new bands were observed because of processing by Dicer; however, bands were observed at the same time in similar positions to those observed in the absence of Dicer, revealing that the processing rate by Dicer was slower than the processing rates for the Ds RNAs and the other RO RNAs.

4. Inhibition of Expression of the Luciferase Gene by the Lipid-Modified Double-Stranded RNAs The RNA interference effects of the synthesized unmodified double-stranded RNAs and lipid-modified double-stranded RNAs were evaluated using *Renilla* luciferase as a target. HeLa cells (human cervical cancer cells; Institute of Development, Aging and Cancer, Tohoku University) adjusted to $1 \times 10^5$ cells/ml prior to the experiments were seeded on a 96-well plate at 100 µl per well, and incubated at 37° C. overnight. On the following day, the old medium on the well was removed, and a new, antibiotic-free medium was added at 80 µl per well, and a complex solution of a vector expressing the firefly and *Renilla* luciferases (psiCHECK™-2 Vector; Promega) and Lipofectamine™ 2000 (trade name; Invitrogen) was added at 10 µl per well containing the HeLa cells. The expression vector was adjusted to 0.02 µg per well, and Lipofectamine™ 2000 was adjusted to 0.2 µg per well, and OptiMem (Invitrogen) was used to adjust the volume to a necessary level. To form a complex, the expression vector and Lipofectamine™ 2000 were mixed using OptiMem, and then the mixture was incubated at room temperature for 30 minutes. After the addition of the complex solution, the cells were incubated at 37° C. for 4 hours in the presence of 5% $CO_2$. After incubation, the unmodified double-stranded RNAs and the double-stranded RNAs modified with a lipid at the end, containing an antisense sequence homologous to the gene sequence of the *Renilla* luciferase, were complexed with Lipofectamine™ 2000 (Invitrogen) at final concentrations of 0 nM, 0.2 nM, 0.5 nM, 1 nM, 2 nM, 5 nM, and 10 nM, and 10 µl each of the resulting complex solutions was added to the HeLa cells into which the expression vector was introduced. The final volume per well was 100 µl. The complex solution of each RNA and Lipofectamine™ 2000 was prepared by mixing the aqueous RNA solution at 5 µl per well and a solution of Lipofectamine™ 2000 (0.2 µl) and OptiMem at 5 µl per well, and incubating the mixture at room temperature for 30 minutes. After the RNA introduction, the cells were incubated for 48 hours, and the levels of firefly and *Renilla* luciferase expression were assayed using a Dual-Glo™ Luciferase Assay System (Promega) and a luminometer (MicroLumat LB96p; Berthold), and the inhibitory effects on the *Renilla* luciferase expression were determined based on the level of firefly luciferase expression as a control.

FIG. 5 shows the inhibitory effects on gene expression attained when the concentration of the unmodified double-stranded RNAs and lipid-modified double-stranded RNAs was 0.2 nM. As a result, it was found that when double-stranded RNAs containing a blunt end on the 5' end side of the sense strand, such as Ds RNAs and RO RNAs, were modified with a lipid, these double-stranded RNAs demonstrated RNA interference effects dramatically improved over the effects provided by the double-stranded RNAs that had the same structure but were not modified with a lipid. It was also found that such high RNA interference effects were attained, irrespective of the strand length or position of the dangling end in the RO RNA, by modifying the 5' end of the sense strand with a lipid, as compared with the unmodified RO RNA with the same structure. These results led to a new finding that the RNA interference effects can be dramatically improved by modifying with a lipid the 5' end of the sense strand of RNA interference molecules containing a blunt end on the 5' end side of the sense strand, such as DS RNAs and RO RNAs. Furthermore, si 21A2C16/21B and si 21A2C12/21B, in which the 5' end of the sense strand of 21 nt siRNA was modified with a lipid, were also found to demonstrate RNA interference effects greater than the effects provided by the unmodified 21 nt siRNA.

5. RNA Interference Effects of Lipid-Modified Double-Stranded RNAs Targeting the Luciferase Genes (Without Using a Gene Transfection Reagent Lipid-modified double-stranded RNAs were transfected into cells alone without using any gene transfection reagents such as Lipofectamine™ 2000 or the like, and evaluated whether or not they demonstrated RNA interference effects.

HeLa cells (human cervical cancer cells; Institute of Development, Aging and Cancer, Tohoku University) adjusted to $1 \times 10^5$ cells/ml prior to the experiments were seeded on a 96-well plate at 100 µl per well, and incubated at 37° C. overnight. On the following day, the old medium on the well was removed, a new, antibiotic-free medium was added at 80 µl per well, and a complex solution of a vector expressing the firefly and *Renilla* luciferases (psiCHECK™-2 Vector; Promega) and Lipofectamine™ 2000 (trade name; Invitrogen) was added at 10 µl per well containing the HeLa cells. The expression vector was adjusted to 0.02 µg per well, and Lipofectamine™ 2000 was adjusted to 0.2 µl per well; OptiMem (Invitrogen) was used to adjust the volume to a necessary level. To form a complex, the expression vector and Lipofectamine™ 2000 were mixed using OptiMem, and then the mixture was incubated at room temperature for 30 minutes. After the addition of the complex solution, the cells were incubated at 37° C. for 4 hours in the presence of 5% $CO_2$.

Each well was then washed with 100 µl of the medium three times to remove Lipofectamine™ 2000 from the well. A medium containing 90 µl of antibiotics was subsequently added to the cells, and the unmodified double-stranded RNAs and the lipid-modified double-stranded RNAs, containing an antisense sequence homologous to the gene sequence of the *Renilla* luciferase, were adjusted with OptiMem to prepare samples at final concentrations of 0 nM, 25 nM, 50 nM, 100 nM, 200 nM, 400 nM, 600 nM, 800 nM, and 1 µM, and 10 µl each of the resulting samples was added to the cells, which were then incubated at 37° C. for 48 hours. The levels of firefly and *Renilla* luciferase expression were assayed using a Dual-Glo™ Luciferase Assay System (Promega) and a luminometer (MicroLumat LB96p; Berthold). As comparisons, the unmodified 21 nt siRNA (si 21A2/21B) and 27 nt dsRNA (Ds 27A1/27B) were also evaluated for their RNA interference effects under the same conditions as described above.

The RNA interference effects were determined by evaluating the level of *Renilla* luciferase expression based on the level of firefly luciferase expression as a control. FIG. 6A shows the results for si 21A2/21B, Ds 27A1/27B, and Ds 27A1C16/27B when the final concentration was from 50 nM to 1 µM and FIG. 6B shows the results for Ds 23A1/23B and Ds 23A1C16/23B when the final concentration was from 25 nM to 800 nM. As a result, it was revealed that Ds 27A1C16/27B and Ds 23A1C16/23B modified with palmitic acid at the 5' end region of the sense strand suppressed the *Renilla* luciferase expression, dependently upon the concentration of the double-stranded RNA; hence, these double-stranded RNAs, because they were modified with palmitic acid, were transfected into the cells alone and thereby produced RNA interference reactions. On the other hand, the unmodified double-stranded RNAs (si 21A2/21B, Ds 27A1/27B, and Ds 23A1/23B) did not demonstrate significant gene expression inhibitory effects even at high concentrations. This further confirmed that the double-stranded RNAs modified with palmitic acid had markedly superior cellular uptake efficiency, and demonstrated an excellent ability to inhibit gene expression without using a gene transfection reagent.

6. Evaluation of the Cellular Uptake efficiency of Lipid-Modified Double-Stranded RNAs HeLa cells (human cervical cancer cells; Institute of Development, Aging and Cancer, Tohoku University), A549 cells (human lung cancer cells; Institute of Development, Aging and Cancer, Tohoku University), and SH10-TC cells (human stomach cancer cells; Institute of Development, Aging and Cancer, Tohoku University), adjusted to $1 \times 10^5$ cells/ml prior to the experiments, as well as Jurkat cells (acute lymphatic leukemia cells; Institute of Development, Aging and Cancer, Tohoku University) and K-562 cells (chronic myelogenous leukemia cells), adjusted to $2 \times 10^5$ cells/ml prior to the experiments, were seeded on 24-well plates at 1 ml per well, and the cells were incubated in a medium containing 10% fetal bovine serum (FBS; Sanko Junyaku, Inc.) and antibiotics at 37° C. in the presence of 5% $CO_2$. Regarding the antibiotic and medium used herein, the antibiotic was an streptomycin for all cells, the medium was an MEM medium (Invitrogen) for the HeLa cells, and an RPMI-1640 (Invitrogen) medium for the other cells. Prior to the transfection of fluorescently labeled oligonucleotides, these media were replaced with an antibiotic-free medium (450 µl). Oligonucleotides labeled with 6-FAM at the 5' end region of the 27 nt antisense strand were used as fluorescently labeled oligonucleotides, and the oligonucleotides were paired with the unmodified 27 nt sense strand or the 27 nt sense strand modified with a lipid at its 5' end region to form double strands. The cellular uptake efficiency experiments were performed as follows. To form a complex of the fluorescently labeled oligonucleotides and Lipofectamine™2000 (Invitrogen), 50 µl of a mixed solution obtained by combining 25 µl of a mixed solution of 10 µl of a 10 µM aqueous fluorescently labeled oligonucleotide solution and 15 µl of the OptiMem solution with 25 µl of a mixed solution of 2 µl of the Lipofectamine™ 2000 (Invitrogen) solution and 23 µl of the OptiMem solution was incubated at room temperature for 30 minutes. When Lipofectamine™ 2000 (Invitrogen) was not used (Section F in FIG. 7; −LF2000), the OptiMem solution was used in place of 2 µl of the Lipofectamine™ 2000 solution used under the conditions of forming a complex described above, and samples were prepared according to the same procedure as above. The resulting 50 µl of the fluorescently labeled oligonucleotide complex was added into 450 µl of the cells prepared above (the final concentration of the double-stranded RNAs: 200 nM), and incubated at 37° C. for 4 hours in the presence of 5% $CO_2$. The cells were subsequently washed with PBS (−) or the medium three times, and the cellular uptake efficiency of the double-stranded RNAs was evaluated using a confocal fluorescence laser microscope and flow cytometry.

In the evaluation using a confocal fluorescence laser microscope, a Radiance 2000 system (Bio Rad) was used, and fluorescence was observed using an argon laser. In the flow cytometry, the cellular uptake efficiency per 10,000 cells counts was measured using a coulter EPICS XL cytometer (Beckman coulter). XL EXPO32™ software (Beckman coulter) was used in the flow cytometric analysis.

The results are shown in FIGS. 7-1 to 7-3. Section F (−LF2000) in FIG. 7-3 shows the results when Lipofectamine™ 2000 was not used, and Sections A to E (+LF2000) in FIGS. 7-1 to 7-3 show the results when Lipofectamine™ 2000 was used as a gene transfection reagent. Section A in FIG. 7-1 shows the results of the cellular uptake efficiency of the various double-stranded RNAs into HeLa cells, using Lipofectamine™ 2000 as a gene transfection reagent; Section B in FIG. 7-1 shows the results for A549 cells; Section C in FIG. 7-2 shows the results for SH10-TC cells; Section D in FIG. 7-2 shows the results for K-562 cells; and Section E in FIG. 7-3 shows the results for Jurkat cells. Section F in FIG. 7-3 shows the results of the cellular uptake efficiency of the various double-stranded RNAs into HeLa cells without using a commercially available gene transfection reagent. Consequently, the transfection of the unmodified double-stranded RNA and lipid-modified double-stranded RNAs into all of the cells (HeLa cells, A549 cells, SH10-TC cells, Jurkat cells, and K-562 cells) was confirmed in the presence of Lipofectamine™ 2000. Particularly with Ds 27A1C16/27B modified with palmitic acid at the 5' end of the sense strand, very high cellular uptake efficiency was observed using a confocal fluorescence laser microscope and flow cytometry, as compared with the unmodified double-stranded RNA and the double-stranded RNA modified with a lauric acid. In addition, the observation using a confocal fluorescence laser microscope suggested that the double-stranded RNA modified with palmitic acid was actively localized into the cytoplasm of cells. In the adherent cells (the HeLa cells, A549 cells, and SH10-TC cells) in particular, this uptake efficiency was notably apparent. Furthermore, the flow cytometric analysis confirmed that the double-stranded RNA modified with palmitic acid demonstrated higher cellular uptake efficiency than the unmodified double-stranded RNA also in the presence of Lipofectamine™ 2000. These results led to a new finding that when a double-stranded RNA is covalently linked with a lipid such as palmitic acid or the like at the 5' end region of the sense strand, the double-stranded RNA can demonstrate dramatically improved cellular uptake efficiency, and can be localized into the cytoplasm of cells.

Example 2

Inhibitory Effects of 5' Lipid-Modified Double-Stranded RNAs on the VEGF Gene Expression 1. Synthesis of Lipid-Modified Double-Stranded RNAs Targeting the VEGF Gene 1-1. Sequences of Sense Strands and Antisense Strands Double-stranded RNAs containing a 27- or 21-base-long sense strand and a 27- or 21-base-long antisense strand were designed having a sequence homologous to VEGF (the vascular endothelial growth factor) and capable of suppressing the expression of the VEGF gene. The following experiments were conducted using these double-stranded RNAs. The 27 nt dsRNA is a completely double-stranded RNA not containing a dangling end (a single-stranded region) (i.e., a double-stranded RNA containing blunt ends on both of the 5' and 3' end sides of the sense strand), and the 21siRNA is a double-stranded RNA containing 2 base dangling ends on the 3' ends of both of the sense and antisense strands. The sequences of the 27 nt dsRNA and 21siRNA used are as follows.

```
27nt dsRNA:
                                              (SEQ ID NO: 10)
sense strand:    5'-CUUCCUACAGCACAACAAAUGUGAAUG-3'
v27A:

(SEQ ID NO: 11)
antisense        3'-GAAGGAUGUCGUGUUGUUUACACUUAC-5'
strand: v27B:

21 siRNA:
                                              (SEQ ID NO: 12)
sense strand:    5'-UCCUACAGCACAACAAAUGUG-3'
v21A:

(SEQ ID NO: 13)
antisense        3'-GAAGGAUGUCGUGUUGUUUAC-5'.
strand: v21B:
```

1-2. Synthesis of Lipid-Unmodified Double-Stranded RNAs Targeting the VEGF Gene

The above-mentioned sense strands and antisense strands were annealed in the same manner as Example 1 to form double strands, thereby producing lipid-unmodified double-stranded RNAs. The formation of the double strands was confirmed by 20% acrylamide gel electrophoresis, according to the same procedure as Example 1.

1-3. Synthesis of Lipid-Modified Double-Stranded RNAs Targeting the VEGF Gene

Lipid-modified double-stranded RNAs in which a lipid was linked to the 5' end of the sense strands of the above-mentioned double-stranded RNAs capable of inhibiting the expression of the VEGF gene were synthesized. In the lipid-modified double-stranded RNAs, the lipid was covalently attached via an aminoalkyl group (Amino Modifier C6; Glen Research) linked to the 5' end of the above-mentioned sense strand. The lipid-modified single-stranded RNAs (sense strands) were synthesized according to the same procedure as Example 1.

The structural models and yields of the lipid-modified RNAs targeting the VEGF gene are as follows.

v27AC16:

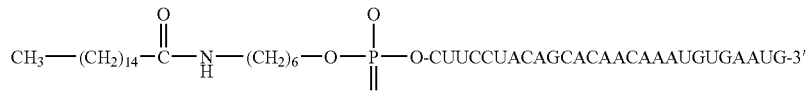

Yield: 45.02% v27AC12:

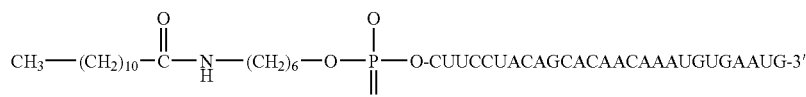

Yield: 33.09% v21AC16:

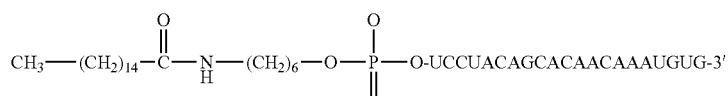

Yield: 21.19% v21AC12:

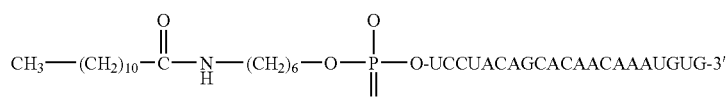

Yield: 47.76%

The resulting lipid-modified sense strands were paired with the antisense strands to produce lipid-modified double-stranded RNAs. The formation of the double strands was confirmed by 20% acrylamide gel electrophoresis according to the same procedure as Example 1. FIG. 8 shows the structures of the lipid-modified double-stranded RNAs. In the lipid-modified RNAs targeting the VEGF gene, the elution times were also substantially the same as in Example 1.

2. Processing by Dicer of the Lipid-Modified Double-Stranded RNAs Targeting the VEGF Gene Processing by recombinant Dicer of the synthesized lipid-unmodified double-stranded RNAs and lipid-modified double-stranded RNAs was evaluated. The Dicer cleavage experiments were performed according to the same procedure as Example 1. The results are shown in FIG. 9.

As a result, with Ds v27AC16/v27B and Ds v27AC12/v27B, bands were observed in similar positions to the unmodified 21siRNA by the action of recombinant Dicer, thus strongly indicating the production of 21-base-long siRNAs containing a dangling end of two bases by Dicer cleavage. These results established that attaching a lipid to the 5' end of the sense strand of 27 nt dsRNA does not hinder Dicer processing. With si v21AC16/v21B and si v21AC12/v21B, on the other hand, no change was observed even in the presence of Dicer, as compared to when Dicer was absent, revealing that they were not processed by Dicer.

3. Inhibition of the VEGF Gene Expression by Lipid-Modified Double-Stranded RNAs 21 nt siRNA with unmodified ends, 27 nt dsRNA with unmodified ends, 27 nt dsRNA modified with a lipid at the 5' end of the sense strand (27 nt dsRNA modified with a lipid at the end), and 21 nt siRNA modified with a lipid at the 5' end of the sense strand (21 nt siRNA modified with a lipid at the end) were evaluated for their inhibitory effects on the VEGF gene expression, using HeLa cells (human cervical cancer cells; Institute of Development, Aging and Cancer, Tohoku University), A549 cells (human lung cancer cells; Institute of Development, Aging and Cancer, Tohoku University), SH10-TC cells (human stomach cancer cells; Institute of Development, Aging and Cancer, Tohoku University), Jurkat cells (acute lymphatic leukemia cells; Institute of Development, Aging and Cancer, Tohoku University), and K-562 cells (chronic myelogenous leukemia cells; Institute of Development, Aging and Cancer, Tohoku University). In addition, double-stranded RNAs not having a gene sequence homologous to the VEGF gene (27 nt dsRNA (Random) and 21 nt siRNA (Random)), as well as lipid-modified double-stranded RNAs in which a lipid was linked to the 5' end of the sense strands of these double-stranded RNAs, were similarly evaluated.

The experiments were performed according to the following procedures. HeLa cells, A549 cells, and SH10-TC cells adjusted to $1\times10^5$ cells/ml prior to the experiments, as well as Jurkat cells and K-562 cells adjusted to $2\times10^5$ cells/ml prior to the experiments, were seeded on 24-well plates at 500 µl per well, and incubated at 37° C. overnight. On the following day, the old medium on the wells was removed, and a new, antibiotic-free medium was added at 450 µl per well. An MEM medium was used for the HeLa cells, and a PRMI-1640 medium was used for the other cells. A complex of the unmodified or lipid-modified double-stranded RNAs (25 µl) containing an antisense sequence homologous to the gene sequence of VEGF with the Lipofectamine™ 2000 solution (Invitrogen) (25 µl) was formed, and then 50 µl each of the double-stranded RNA solutions was added to 450 µl of the above-mentioned cells. The final volume per well was 500 µl. The complex solution of each RNA and the Lipofectamine™ 2000 solution was prepared by mixing the aqueous RNA solution at 25 µl per well and a solution of Lipofectamine™ 2000 (2 µl) and OptiMem at 25 µl per well, and incubating the mixture at room temperature for 30 minutes. After the RNA introduction, the cells were incubated at 37° C. for 48 hours in the presence of 5% $CO_2$. After incubation, the cells were washed with PBS (−) three times, and the total RNA in the cells was extracted using an RNeasy Plus Mini Kit (Qiagen).

The RT-PCR reactions were subsequently performed to measure the amount of mRNA in VEGF. A Qiagen OneStep RT-PCR Kit (Qiagen) was used for the RT-PCR reaction, and 5'-CCC TGA TGA GAT CGA GTA CAT CTT-3' (SEQ ID NO: 14) and 5'-ACC GCC TCG GCT TGT CAC-3' (SEQ ID NO: 15) were used as the PCT primers for VEGF. As a control, the GAPDH gene was measured according to the same procedure. 5'-GGAAAGCTGTGGCGTGATG-3' (SEQ ID NO: 16) and 5'-CTGTTGCTGTAGCCGTATTC-3' (SEQ ID NO: 17) were used as the primers for GAPDH. The RT-PCR reactions were performed as follows. The RT (Reverse Transcription) reaction was performed at 50° C. for 30 minutes, and the PCR reaction, which involved repeated 25 to 28 cycles (depending on the cells used) of a double-strand separation reaction at 92° C. for 30 seconds, an annealing reaction at 55° C. for 30 seconds, and an elongation reaction at 68° C. for 45 seconds, was performed. Lastly, incubation was preformed at 68° C. for 10 minutes, the temperature was decreased to 4° C., and the reaction was completed. The reagents, total RNA, primers, and the like used in RT-PCR were prepared according to the reaction conditions of the Qiagen OneStep RT-PCR Kit (Qiagen). After the RT-PCR reactions, 2 µl of a loading die was added, and the RT-PCR products derived from the mRNAs from VEGF and GAPDH were confirmed using 2% agarose gel. The inhibitory effects on gene expression were evaluated by measuring the level of VEGF expression in the cells into which the double-stranded RNAs (both unmodified and modified) were transfected, assuming that the level of expression of the VEGF gene in the control cells (the cells into which the double-stranded RNAs were not transfected) was 100%. The error in the levels of expression among the cells was corrected based on the level of gene expression of the control gene (GAPDH).

FIGS. 10-1 to 10-3 show the results of the RNA interference effects of the unmodified double-stranded RNAs and lipid-modified double-stranded RNAs when VEGF was targeted and the concentration of the double-stranded RNAs was 200 nM. Graph A in FIG. 10-1 shows the inhibitory effects of the unmodified double-stranded RNAs and lipid-modified double-stranded RNAs on the expression of the VEGF gene in the HeLa cells; Graph B in FIG. 10-2 shows the results for the A549 cells; Graph C in FIG. 10-2 shows the results for the SH10-TC cells; Graph D in FIG. 10-3 shows the results for the Jurkat cells; and Graph E in FIG. 10-3 shows the results for the K-562 cells. These results revealed that Ds v27AC16/v27B and Ds v27AC12/v27B, each obtained by modifying the 5' end of the sense strand of the 27-base-long double-stranded RNA (Ds v27A/v27B) with a lipid, as well as si v21AC16/v21B and si v21AC12/v21B, each obtained by modifying the 5' end of the sense strand of the 21-base-long double-strand RNA (si v21A/v21B) with a lipid, possessed very high inhibitory effects on the VEGF gene expression, as compared with the unmodified double-stranded RNAs (si v21A/21B and Ds v27A/v27B). Ds v27AC16/v27B modified with palmitic acid, in particular, demonstrated markedly higher inhibitory effects on gene expression for all of the cells (the HeLa cells, A549 cells, SH10-TC cells, Jurkat cells, and K-562 cells), as compared with the unmodified double-stranded RNAs (si v21A/21B and Ds v27A/v27B). This confirmed that the RNA interference effects can be dramatically improved by modifying double-stranded RNAs with lipids such as palmitic acid and the like. The unmodified double-stranded RNAs and lipid-modified double-stranded RNAs not having a gene sequence homologous to the VEGF gene were also similarly evaluated for their inhibitory effects on gene expression, but none of the double-stranded RNAs demonstrated any significant inhibitory effects on the VEGF gene. These results revealed that the double-stranded RNAs targeted against VEGF used herein inhibited the expression of the target gene in a highly sequence-specific manner, and also suggested that side effects on the cells can be reduced by linking a lipid to the double-stranded RNAs.

BRIEF DESCRIPTION OF THE DRAWINGS

FIG. 7-1 shows the evaluation results of the cellular uptake of the lipid-modified double-stranded RNAs into HeLa and A549 cells in Example 1; wherein "FL" denotes images taken with a fluorescence microscope; "Trans" denotes images taken with a phase contrast microscope in the same field of view as that of the FL images; and "Merge" denotes images in which the FL image and Trans image were superimposed.

FIG. 7-2 shows the evaluation results of the cellular uptake of the lipid-modified double-stranded RNAs into SH10-TC and K562 cells in Example 1; wherein "FL" denotes images taken with a fluorescence microscope; "Trans" denotes images taken with a phase contrast microscope in the same field of view as that of the FL images; and "Merge" denotes images in which the FL image and Trans image were superimposed.

FIG. 7-3 shows the evaluation results of the cellular uptake of the lipid-modified double-stranded RNAs into Jurkat and HeLa cells in Example 1; wherein "FL" denotes images taken with a fluorescence microscope; "Trans" denotes images taken with a phase contrast microscope in the same field of view as that of the FL images; and "Merge" denotes images in which the FL image and Trans image were superimposed.

FIG. 10-1 shows the evaluation results of the RNA interference effects of lipid-modified double-stranded RNAs on the VEGF gene in HeLa cells in Example 2.

FIG. 10-2 shows the evaluation results of the RNA interference effects of lipid-modified double-stranded RNAs on the VEGF gene in A549 and SH10-TC cells in Example 2.

FIG. 10-3 shows the evaluation results of the RNA interference effects of lipid-modified double-stranded RNAs on the VEGF gene in Jurkat and K567 cells in Example 2.

Figure 1:
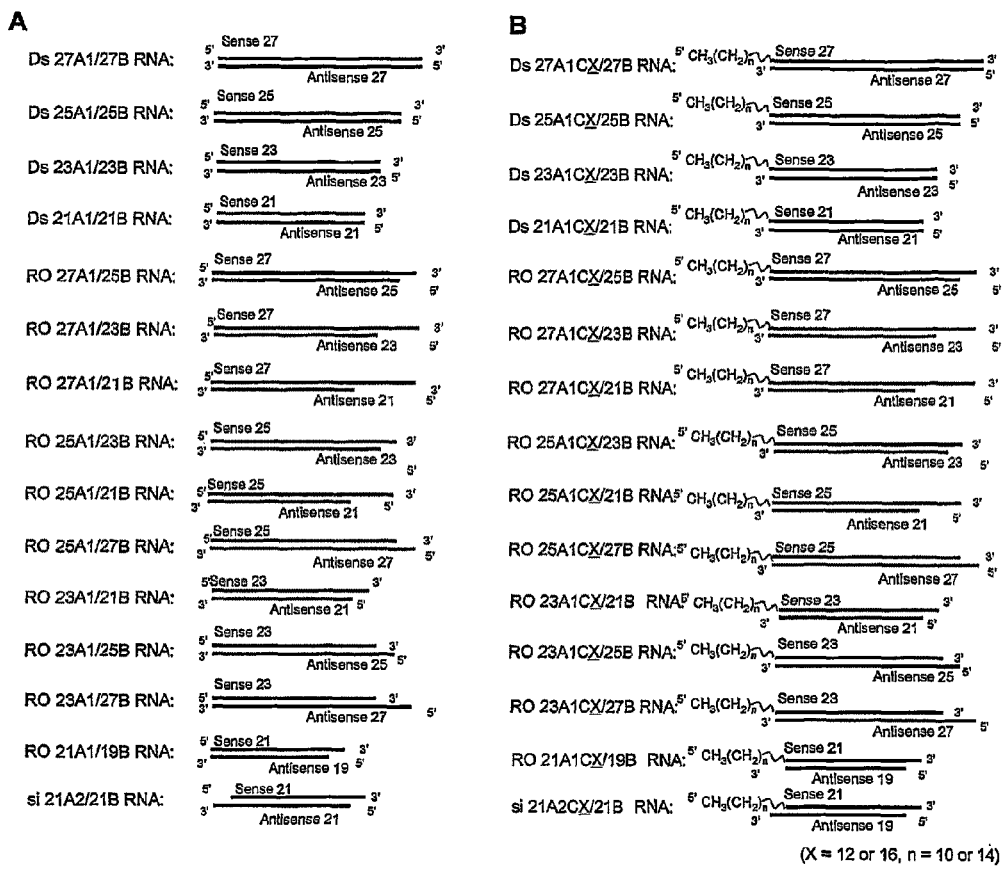
FIG. 1 shows the structures of the unmodified and lipid-modified double-stranded RNAs synthesized in Example 1.
Figure 2:
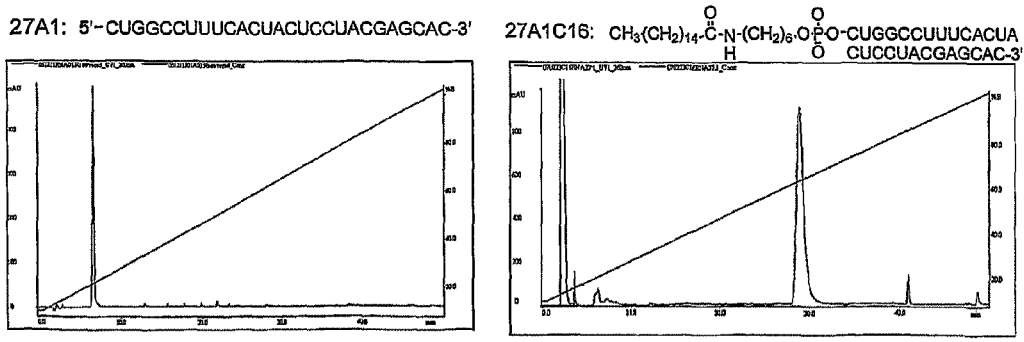
FIG. 2 shows the results of HPLC analysis performed on the lipid-modified single-stranded RNAs in Example 1.
Figure 3:
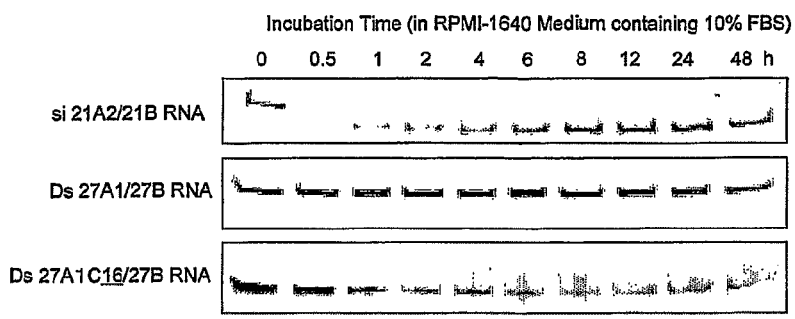
FIG. 3 shows the nuclease resistances of the double-stranded RNAs modified with a lipid at the 5' end, which were measured in Example 1.
Figure 4:
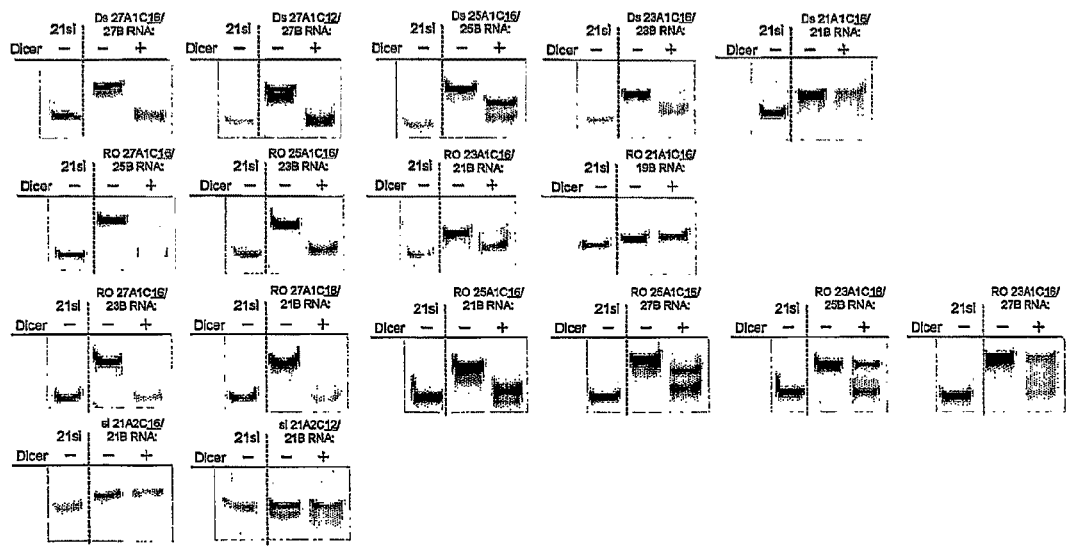
FIG. 4 shows the evaluation results of the processing by Dicer of each of the lipid-modified double-stranded RNAs in Example 1.
Figure 5:
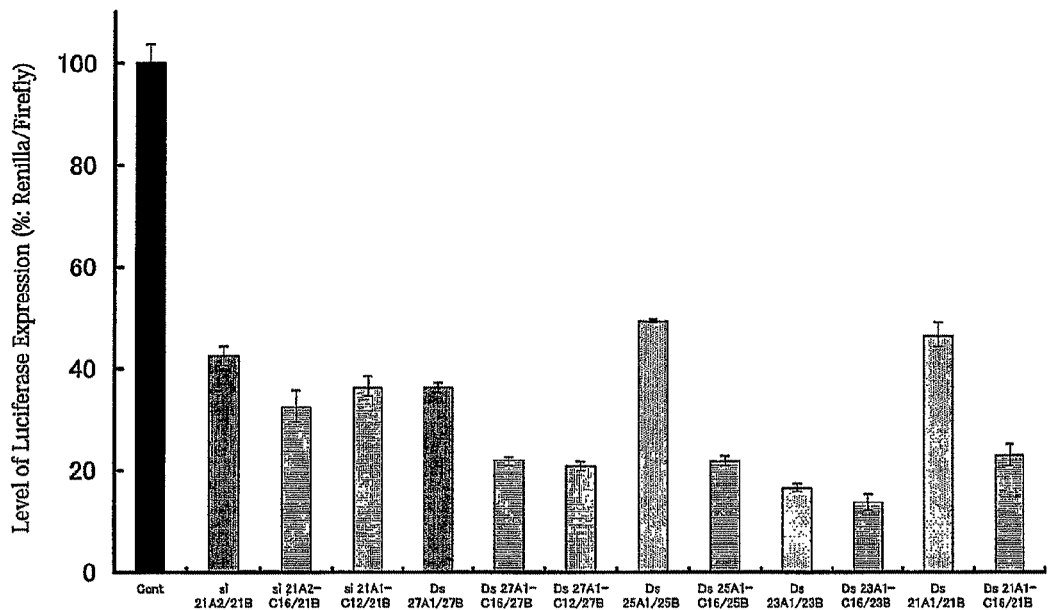
FIG. 5 shows the evaluation results of the RNA interference effects of the lipid-modified 27 nt dsRNAs at a concentration of 0.2 nM in Example 1.
Figure 5:
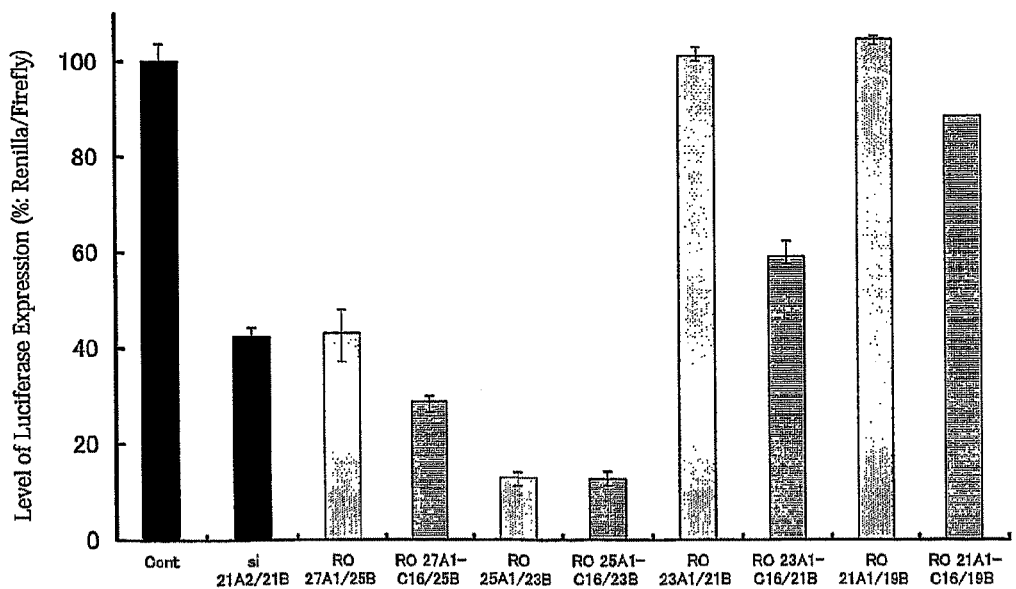
Figure 6:
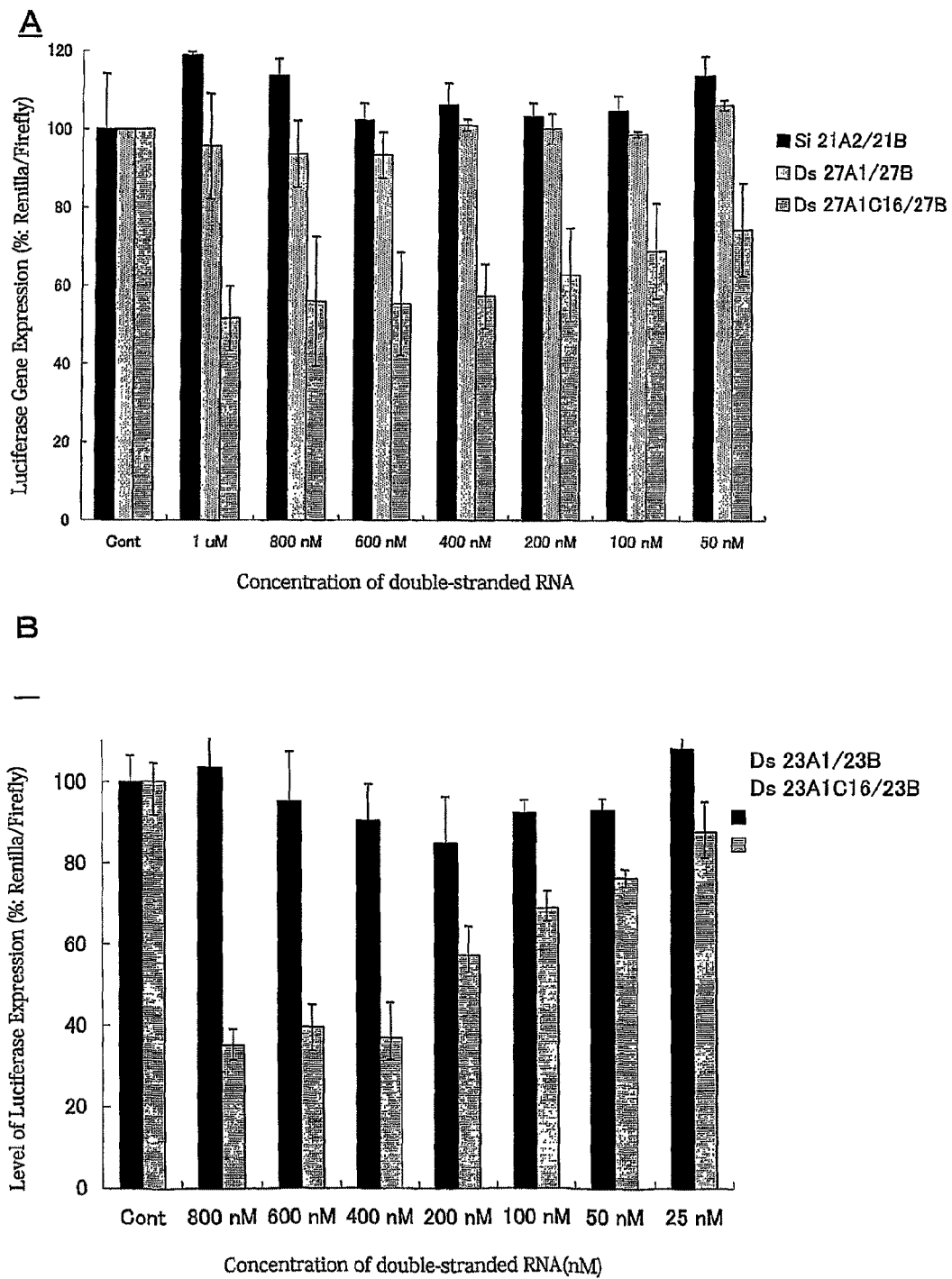
FIG. 6 shows the evaluation results of the RNA interference effects of the double-stranded RNAs modified with a lipid at the 5' end (without using a gene transfer agent) in Example 1.
Figure 7:
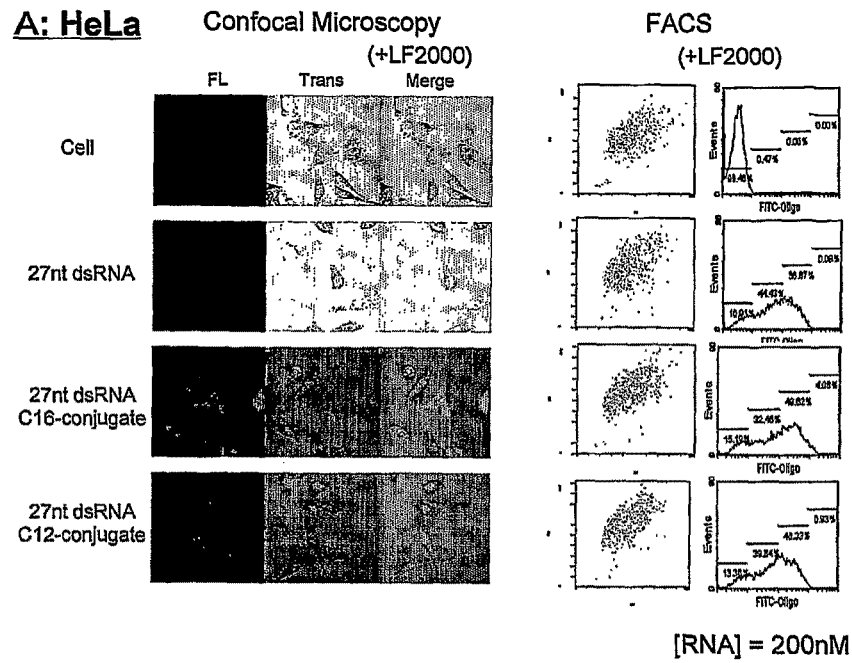
Figure 1:
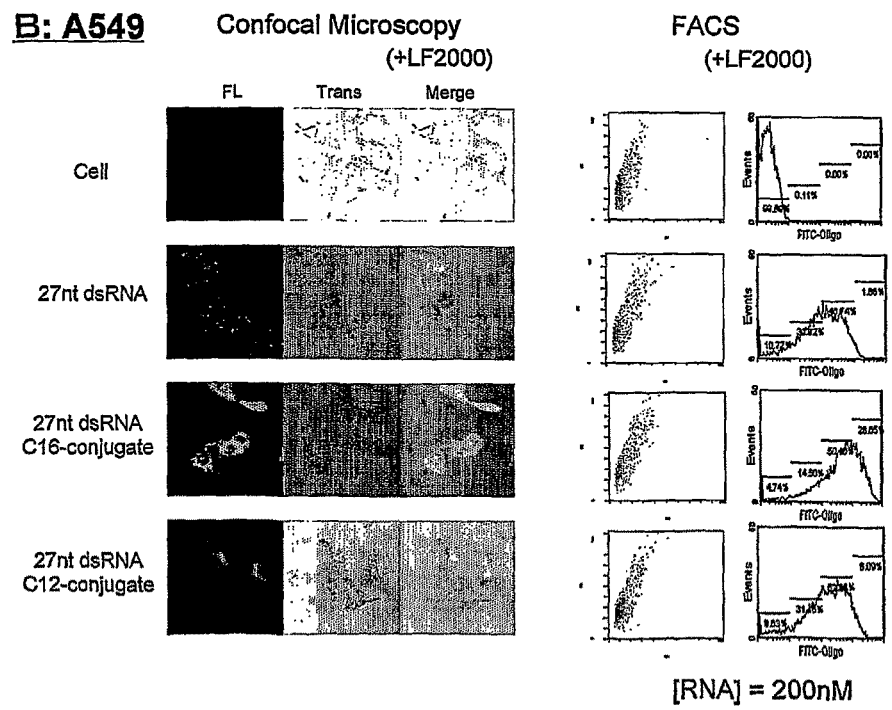
Figure 7:
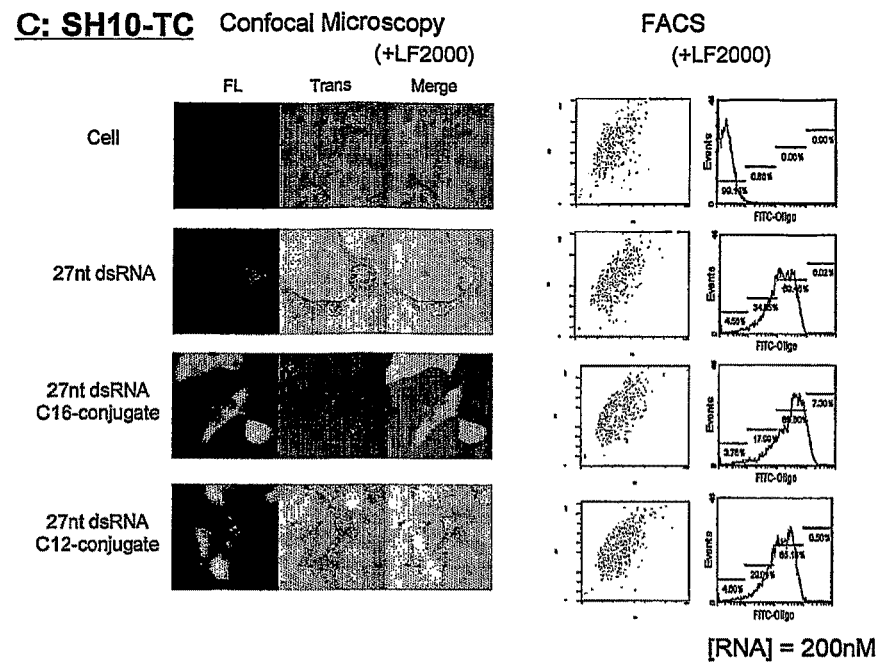
Figure 2:
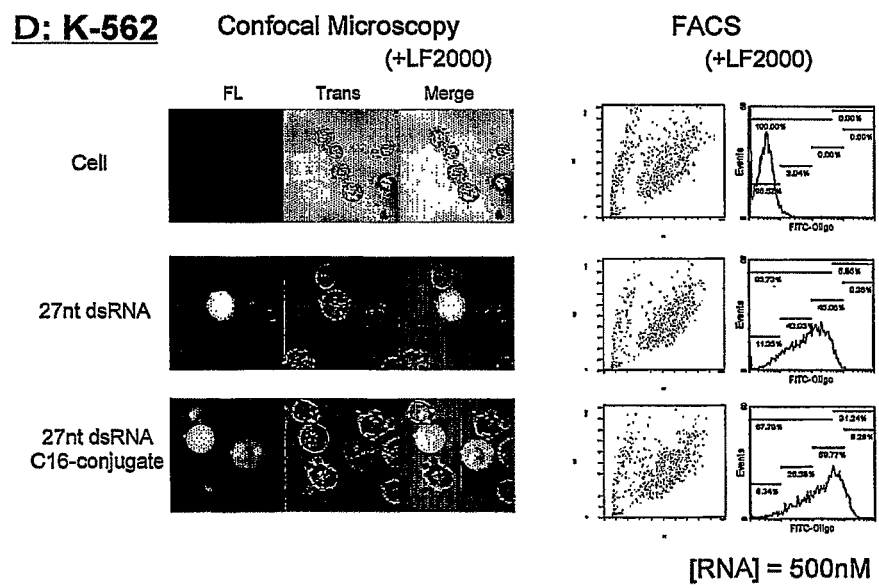
Figure 7:
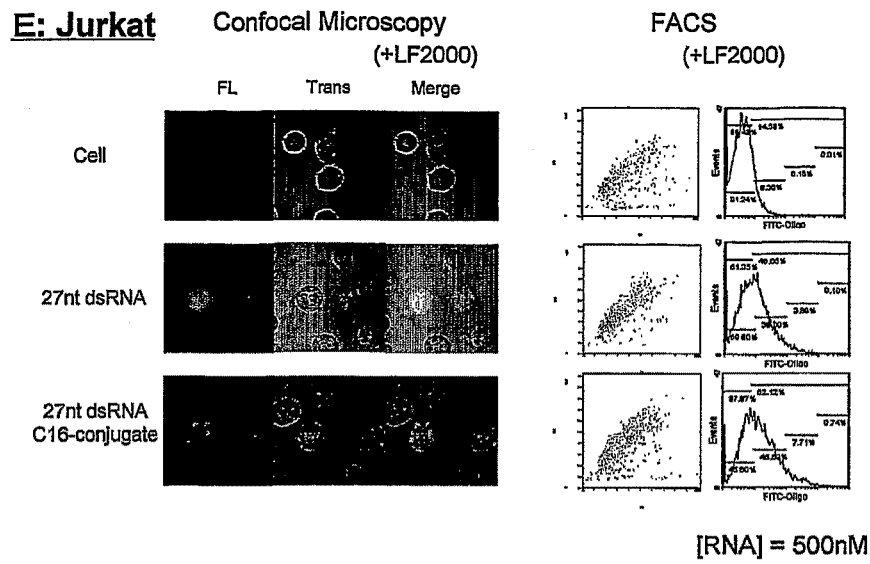
Figure 3:
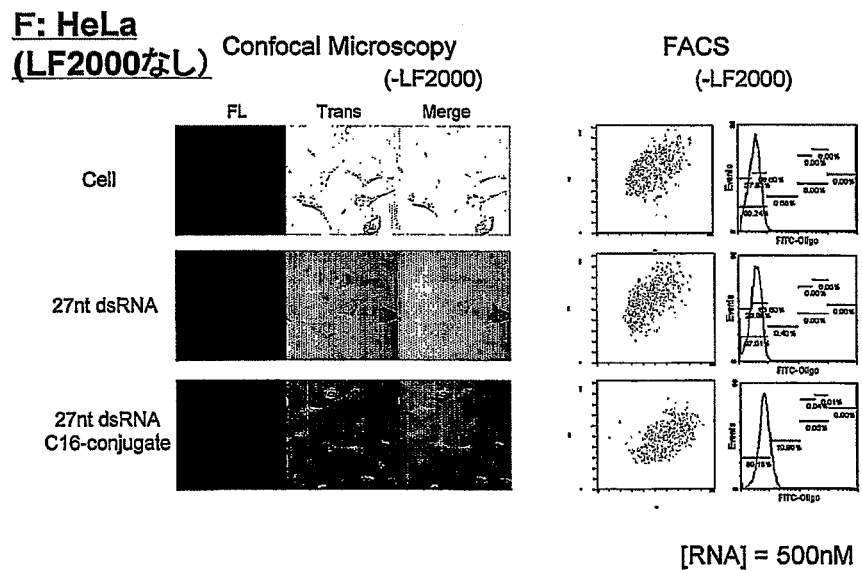
Figure 8:
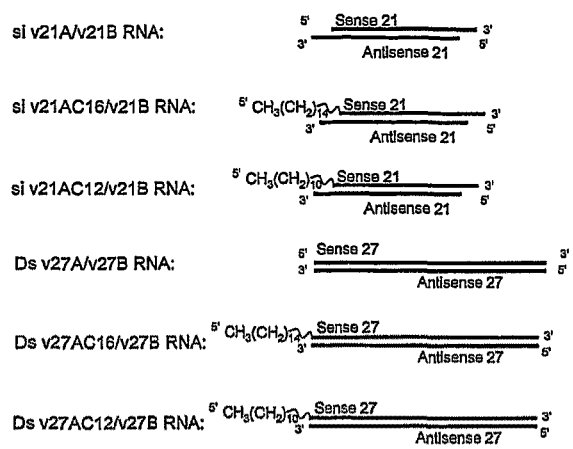
FIG. 8 shows the structures of the unmodified and lipid-modified double-stranded RNAs synthesized in Example 2.
Figure 9:
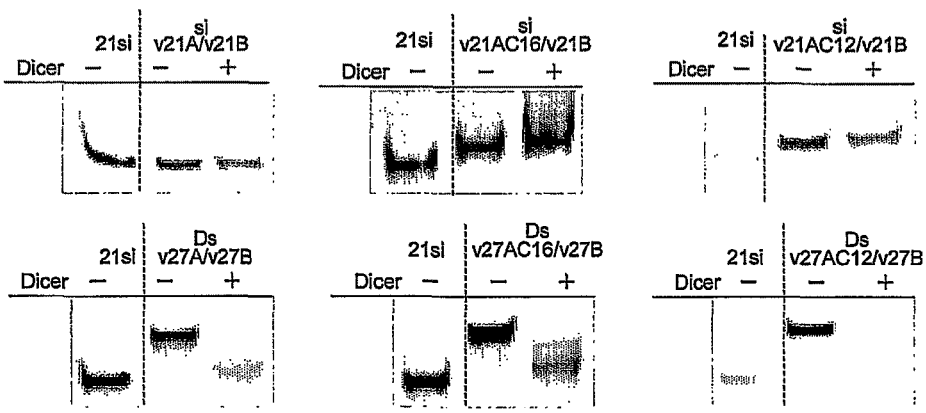
FIG. 9 shows the evaluation results of the processing by Dicer of each of the lipid-modified double-stranded RNAs in Example 2.
Figures 1, 10:
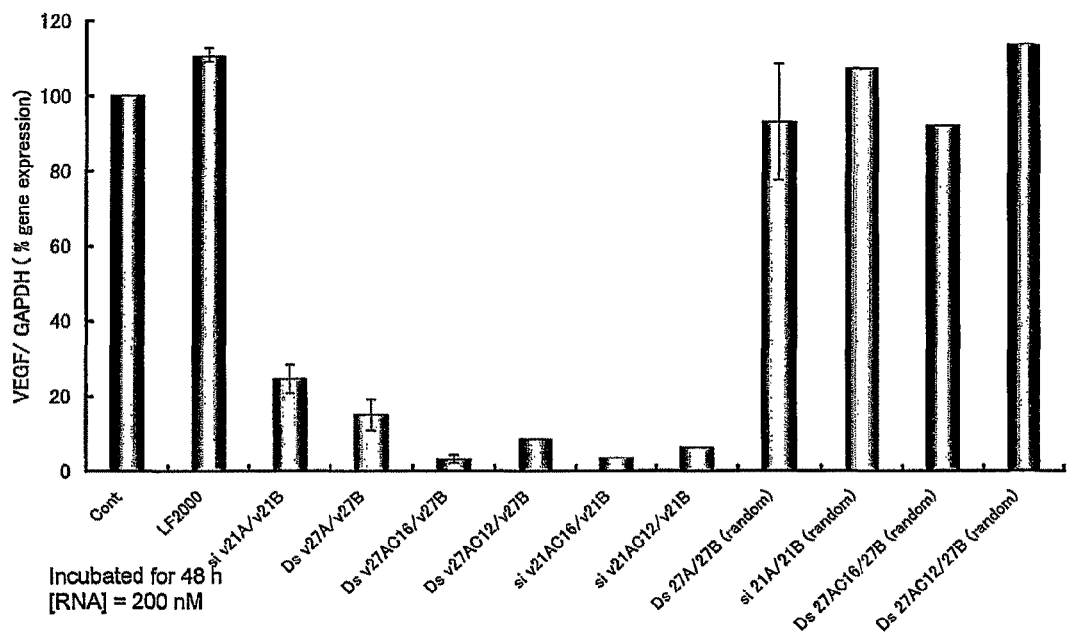
Figure 10:
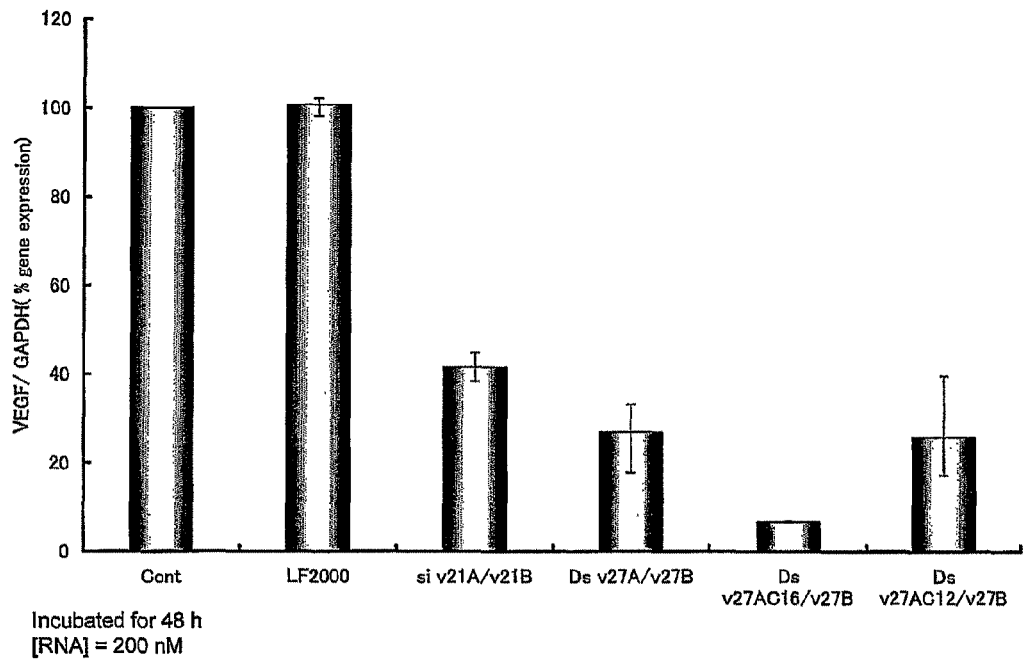
Figure 2:
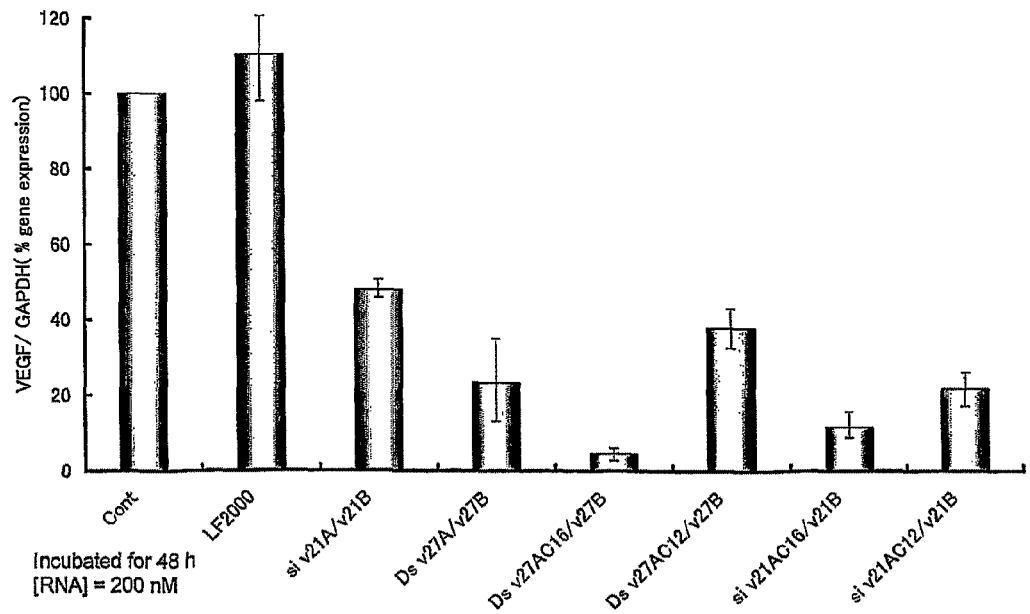
Figure 10:
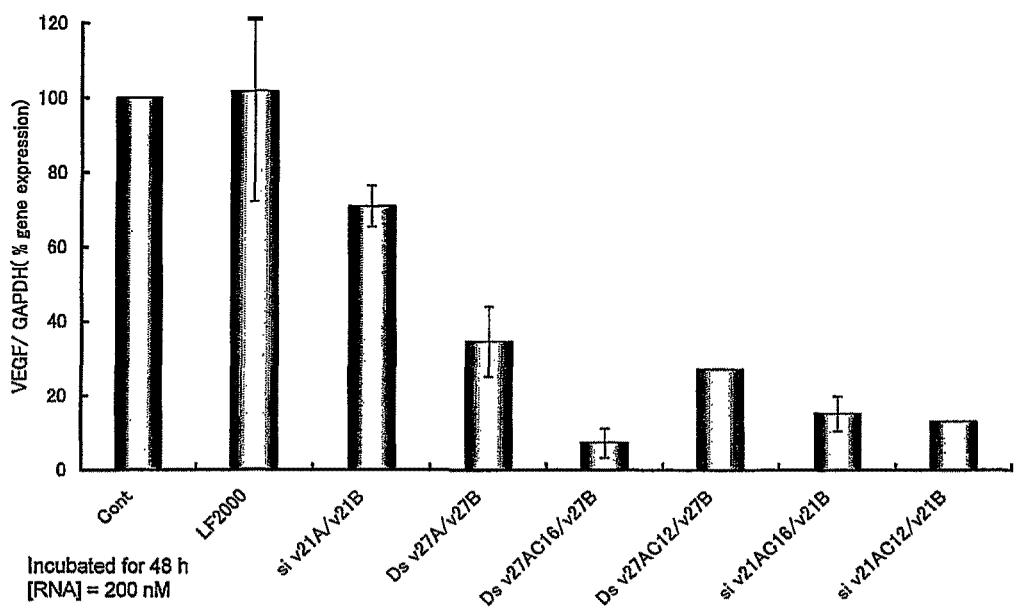
Figure 3:
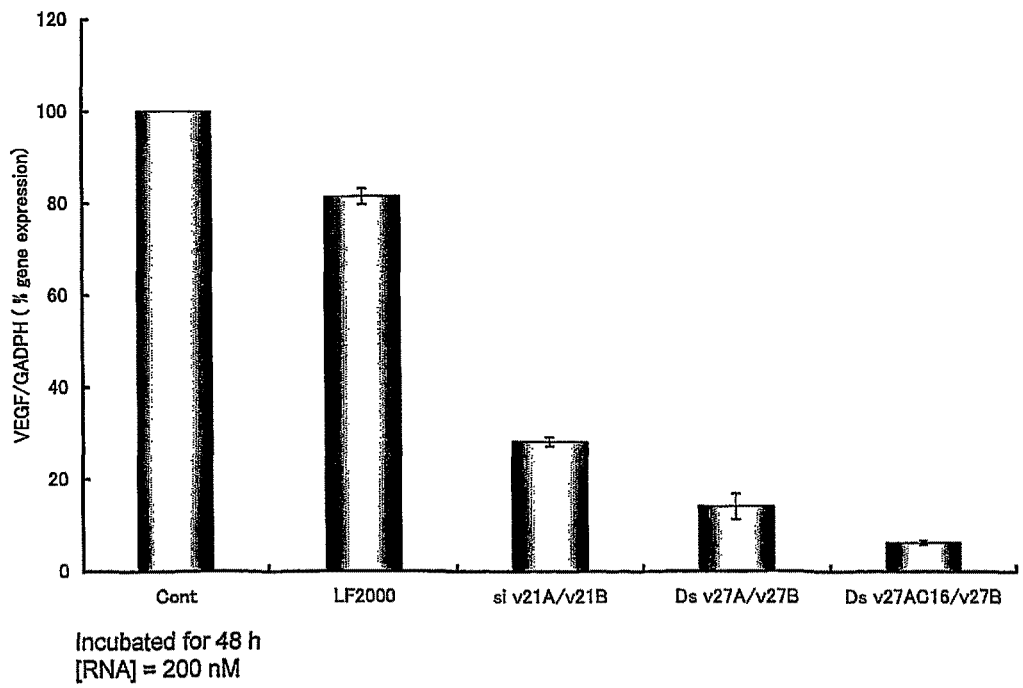

The invention claimed is:

1. A lipid-modified double-stranded RNA comprising:
an antisense strand having a nucleotide sequence complementary to a target sequence in a target gene, and
a sense strand having a nucleotide sequence complementary to the antisense strand,
the double-stranded RNA being blunt-ended on the 5' end side of the sense strand, and being blunt-ended or having a dangling end on the 3' end side of the sense strand, or alternatively the double-stranded RNA having dangling ends on both the 5' and 3' end sides of the sense strand,
the sense strand having a lipid linked to at least one of the first to sixth nucleotides from the 5' end via a linker,
the lipid being a fatty acid having 6 to 50 carbon atoms, and the linker being represented by the structural formula: —NH—$(CH_2)_{n1}$—(L-4), wherein n1 is an integer of 1 to 40.

2. The lipid-modified double-stranded RNA according to claim 1, wherein the sense strand consists of 21 to 27 nucleotides.

3. The lipid-modified double-stranded RNA according to claim 1 which is blunt-ended on both the 5' and 3' end sides of the sense strand, and in which each of the sense and antisense strands consists of 27 nucleotides.

4. The lipid-modified double-stranded RNA according to claim 1 which is blunt-ended on both the 5' and 3' end sides of the sense strand, and in which each of the sense and antisense strands consists of 23 nucleotides.

5. The lipid-modified double-stranded RNA according to claim 1 which is blunt-ended on the 5' end side of the sense strand, the sense strand consisting of 25 nucleotides, and the antisense strand consisting of 23 nucleotides.

6. The lipid-modified double-stranded RNA according to claim 1, wherein each of the sense and antisense strands consists of 21 nucleotides.

7. The lipid-modified double-stranded RNA according to claim 1 wherein the lipid is lauric acid, stearic acid, myristic acid, or palmitic acid.

8. A pharmaceutical composition comprising the lipid-modified double-stranded RNA of claim 1, and a pharmaceutically acceptable base.

9. A method of inhibiting the expression of a target gene comprising introducing a lipid-modified double-stranded RNA of claim 1 into cells to inhibit the expression of the target gene.

* * * * *

```
                        SEQUENCE LISTING

<160> NUMBER OF SEQ ID NOS: 17

<210> SEQ ID NO 1
<211> LENGTH: 27
<212> TYPE: RNA
<213> ORGANISM: Artificial Sequence
<220> FEATURE:
<223> OTHER INFORMATION: Sequence of 27nt 27A1

<400> SEQUENCE: 1
cuggccuuuc acuacuccua cgagcac                                          27

<210> SEQ ID NO 2
<211> LENGTH: 25
<212> TYPE: RNA
<213> ORGANISM: Artificial Sequence
<220> FEATURE:
<223> OTHER INFORMATION: Sequence of 25nt 25A1

<400> SEQUENCE: 2
cuggccuuuc acuacuccua cgagc                                            25

<210> SEQ ID NO 3
<211> LENGTH: 23
<212> TYPE: RNA
<213> ORGANISM: Artificial Sequence
<220> FEATURE:
<223> OTHER INFORMATION: Sequence of 23nt 23A1
```

```
<400> SEQUENCE: 3
cuggccuuuc acuacuccua cga                                          23

<210> SEQ ID NO 4
<211> LENGTH: 21
<212> TYPE: RNA
<213> ORGANISM: Artificial Sequence
<220> FEATURE:
<223> OTHER INFORMATION: Sequence of 21nt 21A1

<400> SEQUENCE: 4
cuggccuuuc acuacuccua c                                            21

<210> SEQ ID NO 5
<211> LENGTH: 21
<212> TYPE: RNA
<213> ORGANISM: Artificial Sequence
<220> FEATURE:
<223> OTHER INFORMATION: Sequence of 21nt 21A2

<400> SEQUENCE: 5
ggccuuucac uacuccuacg a                                            21

<210> SEQ ID NO 6
<211> LENGTH: 27
<212> TYPE: RNA
<213> ORGANISM: Artificial Sequence
<220> FEATURE:
<223> OTHER INFORMATION: Sequence of 27nt 27B

<400> SEQUENCE: 6
gugcucguag gaguagugaa aggccag                                      27

<210> SEQ ID NO 7
<211> LENGTH: 25
<212> TYPE: RNA
<213> ORGANISM: Artificial Sequence
<220> FEATURE:
<223> OTHER INFORMATION: Sequence of 25nt 27B

<400> SEQUENCE: 7
gcucguagga guagugaaag gccag                                        25

<210> SEQ ID NO 8
<211> LENGTH: 23
<212> TYPE: RNA
<213> ORGANISM: Artificial Sequence
<220> FEATURE:
<223> OTHER INFORMATION: Sequence of 23nt 27B

<400> SEQUENCE: 8
ucguaggagu agugaaaggc cag                                          23

<210> SEQ ID NO 9
<211> LENGTH: 21
<212> TYPE: RNA
<213> ORGANISM: Artificial Sequence
<220> FEATURE:
<223> OTHER INFORMATION: Sequence of 21nt 27B

<400> SEQUENCE: 9
guaggaguag ugaaaggcca g                                            21
```

```
<210> SEQ ID NO 10
<211> LENGTH: 27
<212> TYPE: RNA
<213> ORGANISM: Artificial Sequence
<220> FEATURE:
<223> OTHER INFORMATION: Sequence of v27A

<400> SEQUENCE: 10
cuuccuacag cacaacaaau gugaaug                                          27

<210> SEQ ID NO 11
<211> LENGTH: 27
<212> TYPE: RNA
<213> ORGANISM: Artificial Sequence
<220> FEATURE:
<223> OTHER INFORMATION: Sequence of v27B

<400> SEQUENCE: 11
gaaggauguc guguuguuua cacuuac                                          27

<210> SEQ ID NO 12
<211> LENGTH: 21
<212> TYPE: RNA
<213> ORGANISM: Artificial Sequence
<220> FEATURE:
<223> OTHER INFORMATION: Sequence of v21A

<400> SEQUENCE: 12
uccuacagca caacaaaugu g                                                21

<210> SEQ ID NO 13
<211> LENGTH: 21
<212> TYPE: RNA
<213> ORGANISM: Artificial Sequence
<220> FEATURE:
<223> OTHER INFORMATION: Sequence of v21B

<400> SEQUENCE: 13
gaaggauguc guguuguuua c                                                21

<210> SEQ ID NO 14
<211> LENGTH: 24
<212> TYPE: DNA
<213> ORGANISM: Artificial Sequence
<220> FEATURE:
<223> OTHER INFORMATION: PCR primer-1 for VEGF

<400> SEQUENCE: 14
ccctgatgag atcgagtaca tctt                                             24

<210> SEQ ID NO 15
<211> LENGTH: 18
<212> TYPE: DNA
<213> ORGANISM: Artificial Sequence
<220> FEATURE:
<223> OTHER INFORMATION: PCR primer-2 for VEGF

<400> SEQUENCE: 15
accgcctcgg cttgtcac                                                    18

<210> SEQ ID NO 16
<211> LENGTH: 19
<212> TYPE: DNA
<213> ORGANISM: Artificial Sequence
<220> FEATURE:
<223> OTHER INFORMATION: PCR primer-1 for GAPDH
```

```
<400> SEQUENCE: 16
ggaaagctgt ggcgtgatg                                              19

<210> SEQ ID NO 17
<211> LENGTH: 20
<212> TYPE: DNA
<213> ORGANISM: Artificial Sequence
<220> FEATURE:
<223> OTHER INFORMATION: PCR primer-2 for GAPDH

<400> SEQUENCE: 17
ctgttgctgt agccgtattc                                             20
```